(12) United States Patent
Georges et al.

(10) Patent No.: US 11,866,776 B2
(45) Date of Patent: Jan. 9, 2024

(54) METHODS INVOLVING NUCLEIC ACID ANALYSIS OF MILK

(71) Applicant: Université de Liège, Liège (BE)

(72) Inventors: Michel Georges, Liège (BE); Wouter Coppieters, Liège (BE); Latifa Karim, Liège (BE)

(73) Assignee: GESVAL S.A., Liège (BE)

( * ) Notice: Subject to any disclaimer, the term of this patent is extended or adjusted under 35 U.S.C. 154(b) by 0 days.

(21) Appl. No.: 17/040,461

(22) PCT Filed: Mar. 26, 2019

(86) PCT No.: PCT/EP2019/057628
§ 371 (c)(1),
(2) Date: Sep. 22, 2020

(87) PCT Pub. No.: WO2019/185654
PCT Pub. Date: Oct. 3, 2019

(65) Prior Publication Data
US 2021/0024995 A1   Jan. 28, 2021

(30) Foreign Application Priority Data
Mar. 26, 2018 (EP) .................................. 18164063

(51) Int. Cl.
*C12Q 1/6869* (2018.01)
*C12Q 1/6827* (2018.01)
*C12Q 1/6888* (2018.01)

(52) U.S. Cl.
CPC ......... *C12Q 1/6869* (2013.01); *C12Q 1/6827* (2013.01); *C12Q 1/6888* (2013.01); *C12Q 2600/124* (2013.01); *C12Q 2600/156* (2013.01)

(58) Field of Classification Search
CPC ............... C12Q 1/6827; C12Q 1/6888; C12Q 2600/124; C12Q 2600/156; C12Q 1/6869
See application file for complete search history.

(56) References Cited

U.S. PATENT DOCUMENTS

2016/0215331 A1 * 7/2016 Dellaporta ........... C12Q 1/6806

FOREIGN PATENT DOCUMENTS

| EP | 2597159 A1 * | 5/2013 | ........... C12Q 1/6837 |
| KR | 101 603 182 B1 | 3/2016 | |
| WO | 2011/091046 A1 | 7/2011 | |

(Continued)

OTHER PUBLICATIONS

Huang et al. Bioinformatics. 2016. 32(11):1686-1696. (Year: 2016).*

(Continued)

*Primary Examiner* — Joseph G. Dauner
(74) *Attorney, Agent, or Firm* — Polsinelli PC

(57) ABSTRACT

The present application relates to methods for determining the proportion or quantity of DNA contributed by individual animals to a volume of milk collected from a plurality of individual animals, wherein the method employs allele sampling for DNA sequence polymorphisms in DNA extracted from a sample of the volume of milk by shallow whole genome sequencing (SWGS). The present methods are useful for example in detecting mastitis or subclinical mastitis in animals contributing milk to the volume of milk.

23 Claims, 10 Drawing Sheets

(56) References Cited

FOREIGN PATENT DOCUMENTS

WO 2013/079289 A1 6/2013

OTHER PUBLICATIONS

Wang et al. Genome Research. 2013. 23:833-842. (Year: 2013).*
Homer et al. PLoS Genetics. 2008. 4(8):e1000167. (Year: 2008).*
Matukumalli et al. PLoS One. 2009. 4(4):e550. (Year: 2009).*
Blard et al., "Identifying cows with subclinical mastitis by bulk single nucleotide polymorphism genotyping of tank milk." J. Dairy Sci., 95(7):4109-4113 (Jul. 2012).
Browning & Browing, "A unified approach to genotype imputation and haplotype-phase inference for large data sets of trios and unrelated individuals", Am J Hum Genet., 2009, 84(2):210-23.
Browning et al., "A One-Penny Imputed Genome from Next-Generation Reference Panels", Am J Hum Genet., 2018, 103:338-348.
Hogeveen et al., "Economic aspects of mastitis; New developments", N. Z. Vet. J. 2011, 59:16-23.
Howie et al., "Fast and accurate genotype imputation in genome-wide association studies through pre-phasing", Nat Genet., 2012, 44(8):955-959.
Li et al., "MaCH: Using Sequence and Genotype Data to Estimate Haplotypes and Unobserved Genotypes", Genet Epidemiol., 2010, 34(8):816-834.
Marchini & Howie, "Genotype imputation for genome-wise association studies", Nat Rev Genet., 2010, 11:499-511.
Niedringhaus et al., "Landscape of Next-Generation Sequencing Technologies", Anal Chem., 2011, 83(12) 4327-4341.
Sambrook and Russell, "Molecular Cloning: A Laboratory Manual", third edition, Cold Spring Harbor Laboratory Press, Cold Spring Harbor, New York, 1.31-1.38, 2001.
Sharma et al., "A rapid procedure for isolation of RNA-free genomic DNA from mammalian cells", Biotechniques, 1993, 14(2):176-178.
Sims et al., "Sequencing depth and coverage: key considerations in genomic analyses", Nat. Rev. Gen., 2014, 15:121-132.
Catozzi, C. et al. (2017) The microbiota of water buffalo milk during mastitis. PLoS One. 12(9): article No. e0184710, 1-20.
Coppieters, W. et al. (2020) SNP-based quantitative deconvolution of biological mixtures: application to the detection of cows with subclinical mastitis by whole-genome sequencing of tank milk. Genome Research. 30(8): 12-1207.

* cited by examiner

C (cont'd)

B

METHODS INVOLVING NUCLEIC ACID ANALYSIS OF MILK

CROSS REFERENCE TO RELATED APPLICATIONS

This application is a US national phase application of International Application No. PCT/EP2019/057628, filed on Mar. 26, 2019, which claims the benefit of European Patent Application No. 18164063.2, filed Mar. 26, 2018, the disclosure of each of which are explicitly incorporated herein in their entirety by reference.

FIELD

The invention is broadly in the field of animal husbandry and veterinary medicine, and particularly concerns dairy animal health management. The invention provides methods involving nucleic acid analysis of milk, such as tank milk, which can provide valuable information inter alia on the health status of individual animals contributing to the milk.

BACKGROUND

Mastitis is the most common and important health problem in dairying. Losses due to antibiotic treatment and reductions in milk yield and quality amount to approximately 80 EUR per cow per year for the Dutch dairy industry (Hogeveen et al. 2011).

Milk from affected cows is characterised by an increase in the concentration of somatic cells therein—immune cells migrate into the udder and milk—which can be conveniently expressed as 'somatic cell score' (SCS). While normal (healthy) SCS values are less than 100,000 cells/mL milk, SCS may reach millions cells/mL in cows suffering clinical mastitis. Before showing overt symptoms, cows with subclinical mastitis may already have 200,000 cells/mL, the latter SCS value being commonly used as a cut-off value for subclinical mastitis vs. normal health. Cows with subclinical mastitis typically display decreased milk yield and, when added to the tank, their milk detrimentally affects the milk quality of the entire herd. Detection of cows with clinical and subclinical mastitis is therefore paramount.

At present, the most common approach to monitor SCS of individual cows is via milk recording: milk samples from individual cows are collected, for instance monthly, and sent to milk recording centres for analysis of milk components, SCS and bacteriological contamination. However, to control costs, a growing number of dairy farmers either forgo milk recording, or reduce its frequency. Advanced milking machines monitor udder health status by measuring the electrical conductivity of the milk, but are expensive and beyond reach for many farms. There is therefore a pressing need for alternative, costs effective approaches to monitor the mammary health status of farms.

Dairy farms typically comprise tens to hundreds of cows whose milk is stored in large receptacles or 'tanks' prior to daily collection by milk processing factories. EP 2 597 159 and Blard et al. 2012 recently described bulk single nucleotide polymorphism (SNP) genotyping of such tank milk (i.e., without having to perform a separate measurement for each animal) as a way to determine SCS of individual milking cows that have contributed milk to the tank. The method first required all milking cows on a farm to be SNP genotyped (the authors noted that owing to increasing use of Genomic Selection (GS) to select animals including milking cows, the number of farms that SNP genotype all their cows was growing rapidly). SNP genotyping of the tank milk yielded estimates of 'B-allele frequency' (Bfreq) for tens to hundreds of thousands of markers depending on the utilised SNP array. The tank milk's Bfreq for a given SNP reflected the sum (over all cows) of the products of the known B allele count of each cow (g, =0, 1 or 2) and the unknown proportion of contributed DNA ($p_i$). $p_i$'s could be estimated from this ensemble of linear equations using least square or other methods. Combined with the known or estimated milk volumes contributed by individual cows and the known overall SCS in the tank, $p_i$'s could be converted to SCS for each individual cow. The approach of EP 2 597 159 and Blard et al. 2012 using SNP arrays to genotype the tank milk, in combination with SNP-array-produced genotypes for the individual cows contributing to the tank milk, is schematically illustrated in FIG. 1. The number of SNPs needed to achieve adequate accuracy depended on the number of cows on the farm: while tens of thousands of SNPs were sufficient for farms with tens of cows, hundreds of thousands of SNP were needed for farms with several hundreds of cows.

SNP arrays most commonly used for cow genotyping are low-density arrays interrogating several thousand SNPs, such as for example the GoldenGate® Bovine3K Genotyping BeadChip (2,900 SNPs) or the BovineLD v2.0 Genotyping Bead Chip (7,931 SNPs), both developed by Illumina. The rather low number of interrogated SNPs can limit the accuracy of the above-described tank milk genotyping method, especially for large farms (note that average farm size is increasing all over the world and a substantial proportion of the dairy herd already reared in farms counting >250 milking cows in the US, Europe and Australasia). While the authors also proposed to use high density SNP arrays, such as Illumina's 50,000 BovineSNP50 Genotyping BeadChip (current version featuring 53,714 SNPs) or BovineHD Genotyping BeadChip (current version featuring 777,962 SNPs), the use of such high density SNP arrays would significantly increase the cost and thus dramatically reduce the attractiveness of these methods for farmers.

SUMMARY

The present invention addresses problems and/or provides improvements related to bulk nucleic acid analysis of milk, particularly of tank milk. Such methods can allow inter alia to identify cows contributing to the milk which have subclinical or clinical mastitis; and/or to determine whether specific cow(s) did or did not contribute milk to the tank (which may be useful, e.g., to monitor the compliance with exclusion of milk from cows, such as cows undergoing a treatment, to the tank).

Genotyping by DNA sequencing has emerged as a technological alternative to genotyping using SNP arrays. However, generating reliable genotypes that could potentially replace the SNP array-produced genotypes in the above-discussed existing methods for bulk genotyping of tank milk would require high sequence depths and would confront the farmers with unrealistic costs.

Against this backdrop, the present inventors have unexpectedly demonstrated that despite the largely incomplete or 'fuzzy' nature of allele information for most polymorphisms offered by shallow whole genome sequencing (SWGS), SWGS can nonetheless be employed for bulk allele sampling for DNA polymorphisms in milk (e.g., tank milk), such as to allow, in combination with allelic data for said DNA sequence polymorphisms in individual animals contributing to the milk, to estimate the proportion or quantity of DNA contributed by the individual animals to the milk with desirable accuracy. The inventors have demonstrated that bulk SWGS-allele sampling of milk offers valuable results when combined with various methods to generate allelic data for DNA sequence polymorphisms in individual animals contributing to the milk, such as in particular with SNP array genotyping with or without in silico imputation of genotypes at non-interrogated SNPs, or with SWGS-allele sampling data.

Accordingly, an aspect provides a method for determining the proportion or quantity of DNA contributed by individual animals to a volume of milk collected from a plurality of individual animals, the method comprising the steps of:
 a) allele sampling for a plurality of DNA sequence polymorphisms in DNA extracted from a sample of the volume of milk by shallow whole genome sequencing (SWGS); and
 b) determining the proportion or quantity of DNA contributed by the individual animals to the volume of milk, based on the allele sampling for said DNA sequence polymorphisms from step a), and allelic data for said DNA sequence polymorphisms in the individual animals.

A further aspect provides a method for identifying an animal or animals having preclinical or clinical mastitis from a plurality of individual animals contributing milk to a volume of milk, the method comprising the steps of:
 a') determining the proportion or quantity of DNA contributed by the individual animals to the volume of milk by a method comprising allele sampling for a plurality of DNA sequence polymorphisms in DNA extracted from a sample of the volume of milk by SWGS;
 b') determining the concentration of somatic cells in the milk of the individual animals, based on the proportion or quantity of DNA contributed by the individual animals to the volume of milk as determined in step a'); and
 c') identifying an animal or animals as having preclinical or clinical mastitis when the concentration of somatic cells in the milk of said animal or animals as determined in step b') exceeds a predetermined threshold.

These and further aspects and preferred embodiments of the invention are described in the following sections and in the appended claims. The subject-matter of the appended claims is hereby specifically incorporated in this specification.

DESCRIPTION OF EMBODIMENTS

Figure 1:
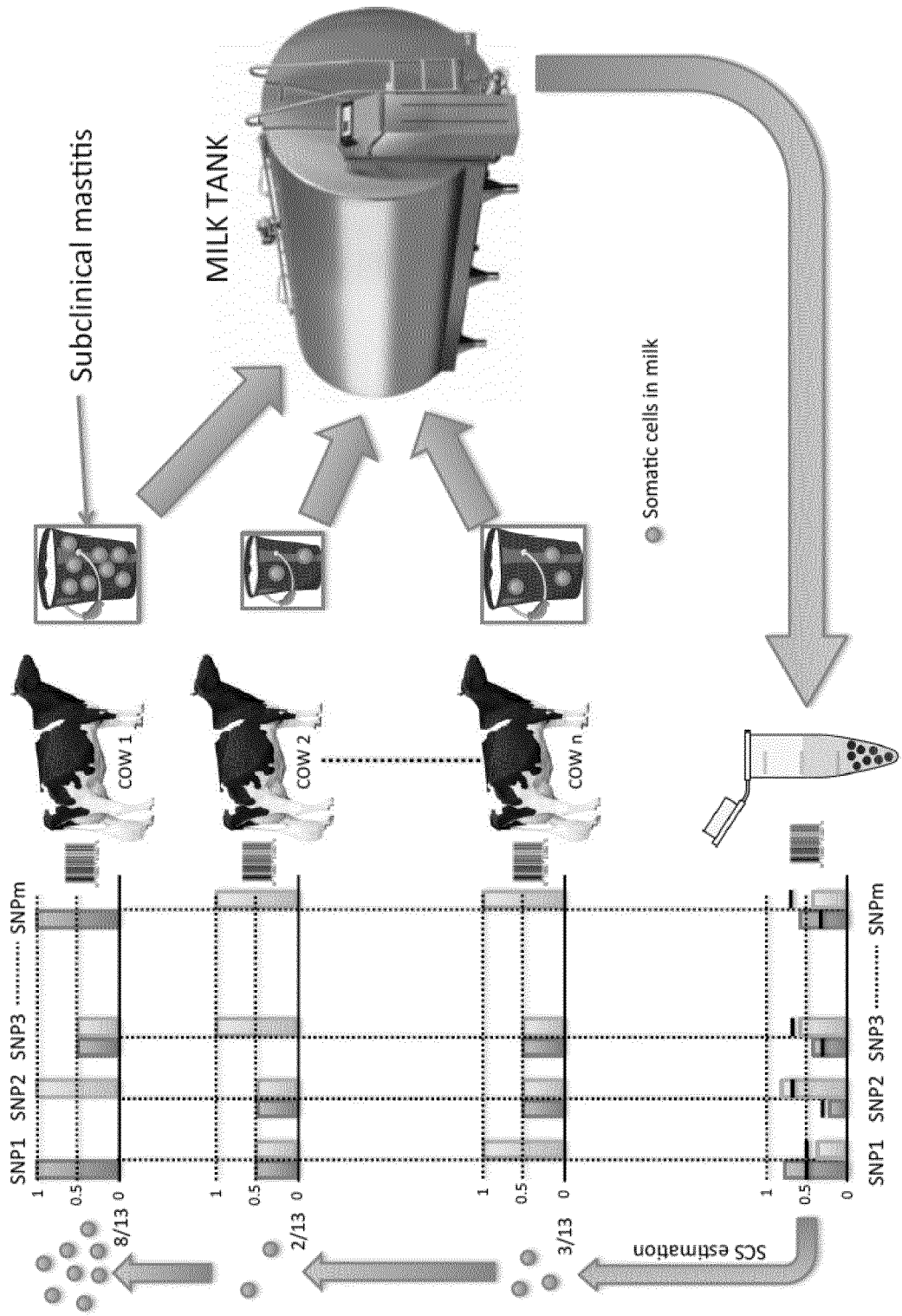
FIG. 1 schematically illustrates the approach proposed in EP 2 597 159 and Blard et al. 2012 for estimating somatic cell score (SCS) and detection of (subclinical) mastitis in individual milking cows that have contributed milk to a milk tank. The approach employed bulk single nucleotide polymorphism (SNP) genotyping of the tank milk by SNP arrays, in combination with SNP-array-produced genotypes for the individual cows contributing to the tank milk.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present inventors have unexpectedly demonstrated that shallow whole genome sequencing (SWGS) can be employed for bulk allele sampling for DNA polymorphisms in milk (e.g., tank milk), such as to allow, in combination with allelic data for said DNA sequence polymorphisms in individual animals contributing to the milk, to estimate the proportion or quantity of DNA contributed by the individual animals to the milk with desirable degree of accuracy and reliability.

The methods embodying the inventors' realisation advantageously allow for example to identify cows contributing to the tank milk which have subclinical or clinical mastitis; and/or to determine whether specific cow(s) did or did not contribute milk to the tank (which may be useful, e.g., to monitor the compliance with exclusion of milk from cows, such as cows undergoing a treatment, to the tank).

Accordingly, an aspect provides a method for determining the proportion or quantity of DNA contributed by individual animals to a volume of milk collected from a plurality of individual animals, the method comprising the steps of:
  a) allele sampling for a plurality of DNA sequence polymorphisms in DNA extracted from a sample of the volume of milk by shallow whole genome sequencing (SWGS); and
  b) determining the proportion or quantity of DNA contributed by the individual animals to the volume of milk, based on the allele sampling for said DNA sequence polymorphisms from step a), and allelic data for said DNA sequence polymorphisms in the individual animals.

A further aspect provides a method for identifying an animal or animals having preclinical or clinical mastitis from a plurality of individual animals contributing milk to a volume of milk, the method comprising the steps of:
  a') determining the proportion or quantity of DNA contributed by the individual animals to the volume of milk by a method comprising allele sampling for a plurality of DNA sequence polymorphisms in DNA extracted from a sample of the volume of milk by SWGS;
  b') determining the concentration of somatic cells in the milk of the individual animals, based on the proportion or quantity of DNA contributed by the individual animals to the volume of milk as determined in step a'); and
  c') identifying an animal or animals as having preclinical or clinical mastitis when the concentration of somatic cells in the milk of said animal or animals as determined in step b') exceeds a predetermined threshold.

The terms "quantity", "amount" and "level" are synonymous and generally well-understood in the art. In certain embodiments, the terms may refer to an absolute quantification or to a relative quantification of an analyte in an object or material of interest. The quantification may entail an analysis of said object or material of interest, or may more typically entail an analysis of a sample of said object or material of interest. An absolute quantity of an analyte in an object or material of interest may be suitably expressed as weight or as molar amount, or more commonly as a concentration, e.g., weight per volume or mol per volume. A relative quantity of an analyte in an object or material of interest may be advantageously expressed relative to a suitable reference variable. In a non-limiting example, the quantity of an analyte in an object or material of interest may be expressed relative to the quantity of a second analyte in said object or material of interest, and may be suitably represented by a weight ratio or molar ratio between said analytes. In a non-limiting example, the quantity of an analyte in an object or material of interest may be expressed relative to the total quantity of all analytes of the same chemical class in said object or material of interest, and may be suitably represented by a weight or molar proportion (fraction or percentage) between said analyte and said total. In yet another non-limiting example, the quantity of an analyte in an object or material of interest may be expressed relative to the quantity of the same analyte in another object or material of interest, and may be suitably represented by a ratio of said quantities or by fold-increase or fold-decrease between said quantities. Performing a relative comparison between first and second variables (e.g., first and second quantities) may, but need not entail determining the absolute values of said first and second variables. For example but without limitation, a quantification method may allow to determine the relative contribution (e.g., weight or molar proportion, fraction or percentage) of each of two or more analytes of the same chemical class to the total quantity of all such analytes in an object or material of interest, without the need to determine or calculate the absolute quantities of either the individual analytes or the absolute total quantity of all such analytes.

Hence, in certain embodiments, the present methods may allow to determine the absolute quantity of DNA contributed by the individual animals to the milk, which may be suitably represented by weight of DNA from a given animal per volume of the milk (w/v), or the concentration of DNA from a given animal in the milk (mol/v).

In more typical embodiments, the present methods determine the relative contribution of the individual animals to the DNA in the milk (more particularly to the pool of DNA from said animals in the milk). The relative contribution of a given animal to the DNA in the milk may be suitably represented by the proportion (fraction or percentage) of the milk DNA which originates from or is attributable to said animal. The present methods may conveniently estimate said proportions as unitless variables.

Hence, in certain preferred embodiments, the present methods determine the proportion of DNA contributed by the individual animals to the volume of milk.

The term "DNA" as used herein denotes deoxyribonucleic acid. The term encompasses DNA when present in cells, when released from cells, as well as when at least partly purified or extracted from such sources. In the present methods, the term particularly denotes DNA from the individual animals, more particularly from somatic cells of the individual animals, even more particularly from nucleated somatic cells of the individual animals. Genomic (nuclear) DNA is particularly intended herein. The term encompasses DNA in any form suitable for adequately carrying out the technical manipulations entailed by the present methods, such as SWGS or SNP array genotyping. By means of an example and not limitation, the term may encompass double-stranded DNA; single-stranded DNA such as denatured DNA; intact DNA; fragmented DNA such as DNA fragmented by application of physical forces (e.g., acoustic shearing, sonication, hydrodynamic shearing) or by enzymatic methods (e.g., DNase I- or other restriction endonuclease, non-specific nuclease, transposase); chemically modified DNA, such as labelled DNA; fragmented DNA to which adapter sequences have been ligated; fragmented DNA ligated into a vector; etc.

The term "animal" as used herein encompasses any milk-producing animals, and particularly refers to lactating female mammals, preferably lactating non-human mammals.

In certain embodiments, the animals are lactating farm animals, particularly lactating female farm mammals. The terms "farm animal" or "farm mammal" encompasses any domestic species of animals or mammals which are kept and raised for profit or for uses such as but not limited to consumption, indirect consumption (i.e., production of food materials such as dairy products), hide production, fur production, breeding, work or as pack animals.

In certain embodiments, the animals are bovid or bovid hybrid. Bovid are cloven-hoofed ruminant mammals belonging to the Bovidae family. Members include, for example, but without limitation wild and domestic cattle, bison (American buffalo), African buffalo, water buffalo, antelopes, gazelles, sheep, goats, muskoxen, and yaks. Hybrids of two different members of the bovid family are included, such as hybrids of American bison or European bison with domestic cattle, domestic cattle/yak hybrids, domestic cattle/water buffalo hybrids, bison/yak hybrids, and the like.

In certain preferred embodiments, the animals are bovine (Bovinae subfamily members), including in particular wild and domestic cattle, bison, African buffalo, water buffalo, and yak. Preferably, the animals may belong to the genus *Bos*.

In certain more preferred embodiments, the animals are cattle, more particularly domestic cattle, such as animals of the species *Bos taurus* or *Bos indicus*, including any cattle breeds, or hybrid cattle. Hence, particularly preferred animals include milking cows.

In certain further preferred embodiments, the animals are buffalo, such as American buffalo or African buffalo.

In certain further embodiments, the animals are sheep, preferably *Ovis aries*.

In certain further embodiments, the animals are goats, preferably *Capra aegagrus hircus*.

The phrase "a volume of milk collected from a plurality of individual animals" broadly denotes any mix or pool of milk collected from such plurality of individual animals. The phrase imposes no restrictions as to the amount or volume (L) of the milk, or as to the receptacle or container in which the milk is kept or stored. For example, any bulk quantity of milk collected from a plurality of animals and pooled, is encompassed.

The term "plurality" as used herein has its ordinary meaning of more than one (>1). Preferably, the term "plurality of individual animals" is intended to encompass typically-sized groups or herds of individual milking animals, such as cattle, hybrid cattle, buffalo, sheep or goats. Hence, in certain embodiments, the phrase "plurality of individual animals" may denote 5 or more ($\geq 5$), $\geq 10$, $\geq 15$, $\geq 20$, $\geq 25$, $\geq 30$, $\geq 40$, $\geq 50$, $\geq 60$, $\geq 70$, $\geq 80$, $\geq 90$, $\geq 100$, $\geq 150$, $\geq 200$, $\geq 250$, $\geq 300$, $\geq 400$, $\geq 500$, $\geq 600$, $\geq 700$, $\geq 800$, $\geq 900$, $\geq 1000$, $\geq 1500$ or $\geq 2000$ individual animals. In certain further embodiments, the phrase "plurality of individual animals" may denote no more than 5000, such as no more than 4000, no more than 3000, no more than 2500, no more than 2000, no more than 1500, or no more than 1000 individual animals. In certain further embodiments, the phrase "plurality of individual animals" may denote between 10 and 25, or between 25 and 50, or between 50 and 100, or between 100 and 250, or between 250 and 500, or between 500 and 1000 individual animals. In certain embodiments, the present methods may be applied to a volume of milk (e.g., tank milk) collected from a plurality of individual animals from a single farm. In certain embodiments, the present methods may be applied to a volume of milk (e.g., tank milk) collected from a plurality of individual animals from two or more farms. In certain embodiments, the present methods may even be applied a volume of milk (e.g., tank milk) at a diary factory, which may typically contain milk collected from a substantial number of farms. Hence, in certain embodiments, the phrase "plurality of individual animals" may also denote $\geq 5000$ individual animals. The term "plurality of individual animals" in the present context may typically but not exclusively denote animals all of which are of the same species. The term may further typically but not exclusively denote animals all of which are of the same subspecies, or of the same variety, or of the same breed. As an illustrative example, the term may denote a plurality of milking Bos taurus cows. As other illustrative examples, the term may denote a plurality of milking Holstein-Friesian cattle, or a plurality of milking Norwegian Red cattle, or a plurality of milking Kostroma cattle, or a plurality of milking Brown Swiss cattle, or a plurality of milking Swedish Red cattle, or a plurality of milking Ayrshire cattle, or a plurality of milking Angeln cattle, or a plurality of milking Guernsey cattle, or a plurality of milking Shorthorn cattle, or a plurality of milking Pie Rouge des Plaines cattle.

In certain other embodiments, term "plurality of individual animals" may denote animals all of which are of the same species or subspecies, but not of the same variety or breed. For example, the plurality may include animals of two or more varieties or breeds, such as of 2-5, e.g., 3 or 4, different varieties or breeds.

In certain embodiments, the volume of milk may refer to tank milk, i.e., milk collected on farms from milking animals and stored in containers conventionally referred to as "milk tanks". Commercial milk tanks typically allow refrigeration and mixing of the collected milk, prior to daily collection by milk haulers. Milk tanks can largely vary in size from 100 litres (L) for the smallest tanks to 150 000 L for silo tanks. Milk silos can typically have capacity of between 25 000 and 150 000 L, whereas intermediate milk tanks can typically have capacity of between 1000 and 10 000 L, and small milk tanks can typically have capacity of between 150 and 3000 L.

Step a) of the present methods involves allele sampling for a plurality of DNA sequence polymorphisms in DNA extracted from a sample of the volume of milk by shallow whole genome sequencing (SWGS).

The term "sample" is as conventionally understood, and in particular refers to a limited quantity, piece or specimen that shows the quality (i.e., is representative or characteristic of the properties) of the whole (e.g., an object or material) from which it was removed or taken. In the present context, a sample may be a certain volume of the milk. The skilled person can select adequate volumes of samples to allow for carrying out the present methods.

DNA, particularly genomic DNA, can be extracted or isolated from DNA-containing samples in ways known in the art. The terms "extracting" or "isolating" with reference to a particular component (such as DNA) of a composition or mixture (such as a sample of milk) encompasses processes or techniques whereby such component is separated from one or more or (substantially) all other components of the composition or mixture. The term does not require absolute purity. Instead, isolating the component will produce a discrete environment in which the abundance of the component relative to one or more or all other components is greater than in the starting composition or mixture. A discrete environment may denote a single medium, such as for example a single solution, dispersion, gel, precipitate, etc. Quantity of nucleic acids may be determined by measuring absorbance A260. Purity of nucleic acids may be determined by measuring absorbance A260/A280, or by agarose- or polyacrylamide-gel electrophoresis and ethidium bromide or similar staining. Conventional techniques for extracting or isolating DNA, particularly genomic DNA, include without limitation organic (phenol-chloroform) extraction, non-organic (proteinase K and salting-out) extraction, ion exchange resin extraction, or silica exchange resin extraction. See inter alia Sambrook and Russell, 2001; and Sharma 1993.

The term "DNA sequence polymorphism" refers to the occurrence of two or more genetically determined alternative sequences or "alleles" at a locus (a polymorphic locus or polymorphic site) in a natural population. Particularly intended herein are sequence polymorphisms in genomic (chromosomal) DNA. A polymorphic locus or site may display without limitation two, three, four, five or more distinct alleles in a natural population. Typically, a locus or site may be deemed polymorphic (and thus useful for genetic analyses) when a minor or rare allele at said locus or site has a frequency of 0.01 (1%) or more, while polymorphic loci with minor allele frequency (MAF) of less than 0.01 (1%), such as for example MAF of 0.001 (0.1%) or more, 0.002 (0.2%) or more, or 0.005 (0.5%) are also applicable in the present methods. Diploid organisms, particularly somatic cells of diploid organisms, may be homozygous or heterozygous for the alleles at a given polymorphic locus or site. For example, where two distinct alleles (A and B) exist at a polymorphic locus or site in a natural population, individuals from the population may be homozygous for the A allele (genotype AA), homozygous for the B allele (genotype BB), or may be heterozygous (genotypes AB or BA).

DNA sequence polymorphisms include in particular but without limitation single nucleotide polymorphisms (SNP or SNPs); restriction fragment length polymorphisms (RFLP); variable number of tandem repeats (VNTR), including 'microsatellites' or short tandem repeats (STR) (such as dinucleotide repeats, trinucleotide repeats or tetranucleotide repeats) and 'minisatellites' (such as repeats of DNA motifs 10-100 bp long); indels (insertion or deletions of more than one nucleotide); hypervariable regions; short interspersed elements (SINE), such as Alu elements; and copy number variations (CNV). Any such DNA sequence polymorphism types or any combinations thereof may be employed in the present methods.

In certain preferred embodiments, the DNA sequence polymorphisms are single nucleotide polymorphisms (SNP). A SNP occurs at a polymorphic site occupied by a single nucleotide, which is the site of variation between allelic sequences. SNPs usually arise due to substitution of one nucleotide for another at the polymorphic site, including transitions (replacement of a purine by another purine, or a pyrimidine by another pyrimidine), and transversions (replacement of a purine by a pyrimidine, or a pyrimidine by a purine). SNPs can also arise due to a deletion of a nucleotide (single nucleotide deletion) or an insertion of a nucleotide (single nucleotide insertion) relative to a reference allele. SNPs are typically the most abundant type of genomic DNA sequence polymorphisms, and their density may range from 1 SNP per several tens of base pairs to 1 SNP per several hundred base pairs, such as for example 1 SNP per 100 base pairs.

There are at present million to tens of millions of reported SNPs for many animals, more particularly milking farm animals, which or subsets of which may be useful in the present methods, such as without limitation:

cattle (www.ncbi.nlm.nih.gov/SNP/snp_batchSearch.cgi?org=9913&type=SNP);
    sheep (www.ncbi.nlm.nih.gov/SNP/snp_batchSearch.cgi?org=9940&type=SNP); or
    goat (www.ncbi.nlm.nih.gov/SNP/snp_batchSearch.cgi?org=9925&type=SNP);

Low and high-density SNP genotyping arrays, which typically contain SNPs evenly spaced across the respective genomes to allow whole genome studies, have also become commercially available for such animals, and may represent preferred subsets of SNPs useful in the present methods, for example but without limitation Illumina's:
GoldenGate® Bovine3K Genotyping BeadChip (2,900 SNPs);
BovineLD v2.0 Genotyping Bead Chip (7,931 SNPs);
BovineSNP50 Genotyping BeadChip (53,714 SNPs);
BovineHD Genotyping BeadChip (777,962 SNPs);
OvineSNP50 BeadChip (54,241 SNPs); or
Goat SNP50 BeadChip (>50,000 SNPs).

The phrase "plurality of DNA sequence polymorphisms" as intended herein broadly denotes any number of polymorphisms that allows the present methods to determine or estimate the result of interest (such as the proportion or quantity of DNA contributed by individual animals to the volume of milk, or the concentration somatic cells in the milk of individual animals) with desirable accuracy. By means of example and without limitation, such accuracy may be expressed as the correlation (r) between the result determined or estimated by the present methods vs. the actual situation (e.g., when DNA quantity or cell concentration in milk is measured for the individual cows separately), calculated by a suitable statistical method (e.g., Pearson, Spearman, or Kendall correlations). Preferably, r may be ≥0.75, more preferably ≥0.80, even more preferably ≥0.85, and still more preferably ≥0.90, such as 0.91, 0.92, 0.93, 0.94, 0.95, 0.96, 0.97, 0.98, 0.99 or even 1.00. By means of another example and without limitation, such accuracy may be represented as the ability to discriminate animals with somatic cell score (SCS) above versus below a certain threshold value measured as $(T_P T_N)/m$, where $T_P$ stands for the number of true positives, $T_N$ for the number of true negatives, and for the total number of animals. The number of polymorphisms may depend on several variables, such as without limitation, the required degree of accuracy, the species, subspecies, variety or breed of the animals, the number of animals contributing to the volume of milk, the depth of the SWGS sequencing, the type and degree of heterozygosity of the polymorphisms, etc.

In certain embodiments, the methods may analyse at least 5000, or at least 10,000, or at least 25,000 or at least 50,000, or at least 100,000, or at least 250,000, or at least 500,000, or at least 750,000, or at least $1.0 \times 10^6$, or at least $2.0 \times 10^6$, or at least $3.0 \times 10^6$, or at least $4.0 \times 10^6$, or at least $5.0 \times 10^6$, or at least $6.0 \times 10^6$, or at least $7.0 \times 10^6$, or at least $8.0 \times 10^6$, or at least $9.0 \times 10^6$, or at least $1.0 \times 10^7$, or at least $1.5 \times 10^7$, or at least $2.0 \times 10^7$ DNA sequence polymorphisms. In certain preferred embodiments, the methods may analyse at least $1 \times 10^5$, preferably at least $5 \times 10^5$, more preferably at least $1 \times 10^6$, even more preferably at least $5 \times 10^6$ or at least $8 \times 10^6$ DNA sequence polymorphisms. In certain embodiments, the methods may analyse less than $2.0 \times 10^7$, or less than $1.5 \times 10^7$, or less than $1.0 \times 10^7$ DNA sequence polymorphisms, such as between $1.0 \times 10^6$ and $1.0 \times 10^7$ DNA sequence polymorphisms, for example about $1.0 \times 10^6$, or about $2.0 \times 10^6$, or about $3.0 \times 10^6$, or about $4.0 \times 10^6$, or about $5.0 \times 10^6$, or about $6.0 \times 10^6$, or about $7.0 \times 10^6$, or about $8.0 \times 10^6$, or about $9.0 \times 10^6$, or about $1.0 \times 10^7$ DNA sequence polymorphisms.

The term "whole genome sequencing" (WGS) broadly denotes methods and approaches in which the entire genome of an organism or genomes of a plurality of organisms (such as in particular, genomic DNA) are entered into the sequencing workflow, typically at a single time. Hence, no steps are included to purposely target or select only a certain part or parts of the genome(s) for sequencing, while excluding or reducing the representation of other parts. The term does not imply that the entire genome of (each) organism is effectively sequenced, but rather denotes that the total genomic DNA in a sample is sequenced to a given depth, without controlled selection or preference for certain parts of the genomic DNA (e.g., for coding sequences or exons). Hence, for example, the chosen depth of whole genome sequencing may be such that not all of the genome(s) are wholly sequenced, but the parts for which no sequence is obtained are distributed substantially randomly or normally. Also, certain parts of the genome(s) may not be readily amenable to sequencing (e.g., repetitive sequences), and such parts may be unintentionally underrepresented in the sequence. Whole genome sequencing allows to sequence the alleles of polymorphisms substantially across or throughout the genome(s), i.e., not limited to polymorphisms in certain part or parts of the genome(s). Various sequencing methodologies, particularly next generation or high-throughput sequencing (NGS), known to the skilled person currently allow for whole genome sequencing of DNA such as genomic DNA. Commercially available examples include Illumina's dye sequencing, pyrosequencing (Qiagen), or SMRT sequencing (PacBio). These approaches employ the well-known whole genome shotgun approach. Third-generation approaches employing for example scanning tunnelling electron microscopy (TEM), fluorescence resonance energy transfer (FRET), single-molecule detection, or nanopore systems. See for example Niedringhaus et al. 2011.

The term "shallow whole genome sequencing" is commonly used in the art to refer to WGS configured to provide for comparatively low or shallow coverage or depth of sequencing. The terms "sequencing depth", "read depth", "sequencing coverage" or "coverage" are used in their conventional sense. In general, the terms denote the average number of times that a given nucleotide in the sequence has been read or sequenced. Hence, for example, sequencing coverage or depth of 0.25, 1.0, 10 or 30 mean that on average each nucleotide will have been sequenced 0.25, 1.0, 10 or 30 times, respectively. Sequencing depth can be conveniently calculated from the length of the sequenced genome (G), the number of reads (N), and the average read length (L), as $N \times L/G$. Sequence coverage is further explained in Sims et al. 2014. By means of an example and without limitation, sequencing depth of SWGS may be 10 or less. In particularly preferred embodiments, sequencing depth of SWGS may be 5 or less, such as about 5.0, about 4.0, about 3.0, or about 2.0, still more preferably 1.0 or less, such as about 1.0, about 0.95, about 0.90, about 0.85, about 0.80, about 0.75, about 0.70, about 0.65, about 0.60, about 0.55, about 0.50, about 0.45, about 0.40, about 0.35, about 0.30, about 0.25, about 0.20, about 0.15, or about 0.10, or about 0.05. In particularly preferred embodiments, sequencing depth of SWGS may be between 0.10 and 1.0, such as between 0.25 and 1.0. Sequencing depth of about 1.0 or lower may be conveniently denoted as "low", whereas sequencing depth of about 0.25 or lower (such as for example between 0.05 and 0.25, or between 0.10 and 0.25) may be conveniently denoted as "ultralow".

The sequencing depth can be selected or optimised based on inter alia the size of the farm, i.e., the number of animals contributing to the milk. For example, in certain embodiments, a sequence depth for the milk of 0.25 can be sufficient to provide a satisfactory accuracy for farms with 100 or less animals (e.g., cows), a sequence depth of 0.5 for farms with 250 or less animals (e.g., cows), a sequence depth of 2.0 for farms with 500 or less animals (e.g., cows), and a sequence depth of 5.0 for farms with 1000 or less animals (e.g., cows).

In certain embodiments, in steps a) and/or step b), or in step a'), of the present methods, the sequencing depth of the SWGS is from 0.10 to 10.0, preferably from 0.25 to 5.0, such as at a sequence depth of about 0.25, about 0.50, about 0.75, about 1.0, about 2.0, about 3.0, about 4.0 or about 5.0. In certain further embodiments, in steps a) and/or step b), or in step a'), of the present methods, the sequencing depth of the SWGS is from 0.25 to 1.0, preferably about 0.25 or about 1.0.

The phrase "allele sampling" for a plurality of DNA sequence polymorphisms by SWGS broadly denotes generating or collecting, by SWGS, at least some information as to the allele(s) for at least some of said plurality of DNA sequence polymorphisms. Due to the shallow sequencing depths of SWGS, the allele information tends to be largely incomplete or 'fuzzy'. For example, the average number of reads for an allele of a SNP would be expected to correspond to the sequencing depth of the SWGS. Hence, a fraction of the polymorphic loci may be covered by no reads, a fraction by only one read, and a fraction by two or more reads. By means of an example and without limitation, based on a Poisson distribution with a mean equal to the sequencing depth:

- for sequencing depth of 1.0, 63% of polymorphic loci would be sampled (i.e., at least one read), whereas 37% of polymorphic loci would not be sampled (i.e., no read), and of the sampled loci, only 1 allele (one read) would be sampled for 58% loci, and 2 or more reads would be sampled for 42% loci; or
- for sequencing depth of 0.25, 22% of polymorphic loci would be sampled (i.e., at least one read), whereas 78% of polymorphic loci would not be sampled (i.e., no read), and of the sampled loci, only 1 allele (one read) would be sampled for 88% loci, and 2 or more reads would be sampled for 12% loci.

Hence, in certain embodiments, allele sampling of DNA sequence polymorphisms by SWGS as intended herein may be low allele sampling (in particular, obtained or obtainable by SWGS sequencing depths of about 1.0 or lower) or may be ultralow allele sampling (in particular, obtained or obtainable by SWGS sequencing depths of about 0.25 or lower, such as for example between 0.05 and 0.25, or between 0.10 and 0.25).

For example, in certain embodiments, between about 10% and about 80% of polymorphic loci will be sampled by at least one read, while between about 90% and about 20% of polymorphic loci will not be sampled (no read). In further embodiments, between about 10% and about 70% of polymorphic loci will be sampled by at least one read, while between about 90% and about 30% of polymorphic loci will not be sampled (no read). In further embodiments, between about 15% and about 65% of polymorphic loci will be sampled by at least one read, while between about 85% and about 35% of polymorphic loci will not be sampled (no read). In further embodiments, between about 20% and about 60% of polymorphic loci will be sampled by at least one read, while between about 80% and about 40% of polymorphic loci will not be sampled (no read). For example, in certain embodiments: about 15%, or about 20%, or about 25%, or about 30%, or about 35%, or about 40%, or about 45%, or about 50%, or about 55%, or about 60%, or about 65%, or about 70%, of polymorphic loci will be sampled by at least one read, while respectively about 85%, or about 80%, or about 75%, or about 70%, or about 65%, or about 60%, or about 55%, or about 50%, or about 45%, or about 40%, or about 35%, or about 30% of polymorphic loci will not be sampled (no read). In certain embodiments, the methods may entail including only polymorphisms sampled by a preselected number of reads (e.g., no more than one read, or no more than 2 reads, or no more than 3 reads) in subsequent analysis.

In certain steps, the allele sampling of said DNA sequence polymorphisms by SWGS in step a) or step a') is low or ultralow allele sampling.

Despite the fact that SWGS may yield no, or incomplete or comparatively inaccurate allelic information for any given polymorphism (e.g., SNP), the present inventors unexpectedly realised that integrating this 'fuzzy' information from allelic sampling by SWGS for a large number, such as hundreds of thousands to millions of polymorphisms, can still be used to generate very useful and accurate estimates on the proportion or quantity of DNA contributed by individual animals to the volume of milk, or the concentration somatic cells in the milk of individual animals.

Step b) of the present methods involves determining the proportion or quantity of DNA contributed by the individual animals to the volume of milk, based on the allele sampling of said DNA sequence polymorphisms from step a), and allelic data for said DNA sequence polymorphisms in the individual animals.

In this context, the term "allelic data" broadly encompasses any quality and quantity of allelic information for said polymorphisms in the individual animals, such as discrete genotypes (i.e., the identity of both alleles present at a polymorphic locus), allelic compositions or dosages, or allele sampling data from SWGS (i.e., SWGS-allele sampling data).

Hence, in certain embodiments, the allelic data for said DNA sequence polymorphisms in the individual animals in step b) comprises or consists of the genotypes or allelic dosages for said DNA sequence polymorphisms in the individual animals and/or SWGS-allele sampling data of said DNA sequence polymorphisms in the individual animals.

In certain embodiments, the allelic data for said DNA sequence polymorphisms in the individual animals in step b) comprises or consists of the genotypes for said DNA sequence polymorphisms in the individual animals.

In certain embodiments, the allelic data for said DNA sequence polymorphisms in the individual animals in step b) comprises or consists of SWGS-allele sampling data of said DNA sequence polymorphisms in the individual animals.

In certain preferred embodiments, the SWGS-allele sampling data in the individual animals in step b) may be from SWGS having sequencing depth of 5 or less, such as about 5.0, about 4.0, about 3.0, or about 2.0, still more preferably 1.0 or less, such as about 1.0, about 0.95, about 0.90, about 0.85, about 0.80, about 0.75, about 0.70, about 0.65, about 0.60, about 0.55, about 0.50, about 0.45, about 0.40, about 0.35, about 0.30, about 0.25, about 0.20, about 0.15, or about 0.10, or about 0.05; or particularly preferably sequencing depth between 0.10 and 1.0, such as between 0.25 and 1.0.

In certain embodiments, the SWGS-allele sampling data in the individual animals in step b) is from low (in particular, obtained or obtainable by SWGS sequencing depths of 1.0 or lower) or ultralow (in particular, obtained or obtainable by SWGS sequencing depths of 0.25 or lower, such as for example between 0.05 and 0.25, or between 0.10 and 0.25) allele sampling by SWGS, as explained elsewhere in this specification.

In certain preferred embodiments, the SWGS-allele sampling data in the individual animals in step b) may be from SWGS having a sequencing depth which is the same or substantially the same as the sequencing depth of the SWGS used for the allele sampling in step a). In this context, "substantially the same" may denote that the respective sequencing depths differ by no more than 0.50, preferably by no more than 0.40, more preferably by no more than 0.30, such as for example, by no more than 0.25, by no more than 0.20, by no more than 0.15, by no more than 0.10, or by no more than 0.05.

The present methods generally suppose pre-existence of the allelic data for said DNA sequence polymorphisms in the individual animals. Such allelic data can be generated in known ways, such as by genotyping or by allele sampling by SWGS (essentially as described above). To this end, DNA extracted from the animals is used, particularly from somatic cells, more particularly genomic DNA from somatic cells, such as for example, DNA extracted from a blood specimen.

The term "genotyping" conventionally denotes the process of determining which alleles at one or more polymorphic sites are present in an analysed DNA sample, such as in a DNA sample from an individual animal. Depending on circumstances, genotyping methods may identify discrete genotypes, or may provide allelic compositions or dosages, such as the relative abundance of the alleles at an interrogated DNA sequence polymorphism. Preferably, genotyping methods may identify discrete genotypes.

Genotyping techniques are routine and generally well-known in the art. By means of an example and without limitation, custom or commercially available genotyping arrays such as SNP genotyping arrays can allow to genotype large numbers of SNPs in parallel. Non-limiting examples of such SNP arrays useful in practicing certain embodiments of the present invention include Illumina's GoldenGate® Bovine3K Genotyping BeadChip (2,900 SNPs), BovineLD v2.0 Genotyping Bead Chip (7,931 SNPs), BovineSNP50 Genotyping BeadChip (53,714 SNPs), BovineHD Genotyping BeadChip (777,962 SNPs), OvineSNP50 BeadChip (54,241 SNPs), or Goat SNP50 BeadChip (>50,000 SNPs). Further genotyping methods include sequencing, such as targeted genome sequencing or whole genome sequencing. Whole genome sequencing (WGS) may be preferred. Preferably, in the context of genotyping, WGS may employ sequencing depths which allow for substantially unambiguous calling of the genotypes, such as for example, sequencing depths of 10 or more, or 20 or more, or 30 or more, such as for example, about 40, about 50, about 60, about 70 or about 80 (e.g., "deep" WGS).

Hence, in certain embodiments, the genotypes for said DNA sequence polymorphisms in the individual animals as used in step b) have been at least in part determined by genotyping arrays such as SNP genotyping arrays, by genome sequencing such as targeted genome sequencing or whole genome sequencing, or by any combination thereof.

In certain preferred embodiments, the genotypes for said DNA sequence polymorphisms in the individual animals as used in step b) have been at least in part determined by genotyping arrays. In certain preferred embodiments, the genotypes for said DNA sequence polymorphisms in the individual animals as used in step b) have been at least in part determined by SNP genotyping arrays.

In certain embodiments, the genotypes for said DNA sequence polymorphisms in the individual animals as used in step b) have been at least in part determined by whole genome sequencing. In certain embodiments, the genotypes for said DNA sequence polymorphisms in the individual animals as used in step b) have been at least in part determined by deep whole genome sequencing.

Typically, such SNP genotyping arrays may be capable of interrogating several thousand SNPs (e.g., at least 2500, at least 5000, or at least 7500 SNPs), several tens of thousands SNPs (e.g., at least 10,000, or at least 25,000, or at least 50,000, or at least 70,000 SNPs), or even several hundreds of thousands SNPs (e.g., at least 100,000, or at least 250,000, or at least 500,000, or at least 750,000 SNPs). However, comparatively lower density SNPs may be less costly and thus more acceptable for farmers. Hence, in certain embodiments, the genotypes for said DNA sequence polymorphisms in the individual animals have been at least in part determined by a SNP genotyping array capable of interrogating 100,000 or less SNPs, preferably 50,000 or less SNPs, more preferably 10,000 or less SNPs. The inventors have demonstrated that in certain embodiments of the present methods, the accuracy of the predictions may be only marginally affected by the type of SNP array that is used (for example, in the data shown in FIG. 2B, 10K SNP arrays performed as well as the 50K).

The genotypes for said DNA sequence polymorphisms in the individual animals may be 'real' genotypes (i.e., experimentally detected genotypes) and/or may be genotypes that are determined by the process of in silico genotype imputation as known in the art (see Marchini & Howie 2010). Genotype imputation involves the statistical inference of unobserved genotypes based on the genotypes experimentally observed in a sample (such as in an individual animal), and using known haplotypes in a population (such as in a native population of animals of the same species, subspecies, variety or breed). Hence, genotype imputation will typically require that a reference population has been previously genotyped with high density SNP arrays or by whole genome sequencing at high depth (e.g., >10), a situation which is becoming increasingly commonplace for livestock, especially for important world breeds (e.g. Holstein-Friesian, Jersey, or Brown Swiss cattle breeds), but reference populations can be readily genotyped for other breeds as well. Software packages for performing genotype imputation are publically available, such as Beagle (Browning & Browning 2009), MaCH (Li et al. 2010), or IMPUTE2 (Howie et al. 2012).

Accordingly, in certain embodiments, the genotypes or allelic dosages for said DNA sequence polymorphisms in the individual animals as used in step b) have been at least in part imputed.

When genotypes are imputed there will exist some uncertainty on the actual underlying genotype. Hence, in imputed data, the allele dosage is frequently not 0, 0.5 or 1, but can somewhat deviate from these values. Such allele dosages can be transformed to genotypes, taking the genotype that has the highest probability. Alternatively, when analysing imputed data, one can employ a method which can accept such allelic dosages or genotypes, thereby potentially gaining some power when the imputed allelic dosages are used instead of the respective most likely genotypes.

Genotype imputation allows to considerably increase the number of polymorphisms for the individual animals which can be used in step b) of the present methods. Given that allele sampling by SWGS in step a) generates information for a very large number (such as hundreds of thousands to millions) of polymorphic sites, genotype imputation can advantageously increase the number of polymorphisms for the individual animals to the same order of magnitude, allowing for more informative statistical analysis.

Hence, in certain embodiments, the allelic data for said DNA sequence polymorphisms in the individual animals in step b) comprises or consists of the genotypes for said DNA sequence polymorphisms in the individual animals, which are in part experimentally detected and in part imputed.

In certain embodiments, the genotypes for said DNA sequence polymorphisms in the individual animals as used in step b) have been in part determined by genotyping arrays such as SNP genotyping arrays, by genome sequencing such as targeted genome sequencing or whole genome sequencing, or by any combination thereof, and in part imputed based on the experimentally determined genotypes.

In certain preferred embodiments, the genotypes for said DNA sequence polymorphisms in the individual animals as used in step b) have been in part determined by genotyping arrays, such as SNP genotyping arrays, and in part imputed based on the experimentally determined genotypes.

By means of an example and not limitation, the genotypes for said DNA sequence polymorphisms in the individual animals as used in step b) may have been in part determined by (SNP) genotyping arrays capable of interrogating several thousand SNPs (e.g., at least 2500, at least 5000, or at least 7500 SNPs), several tens of thousands SNPs (e.g., at least 10,000, or at least 25,000, or at least 50,000, or at least 70,000 SNPs), or even several hundreds of thousands SNPs (e.g., at least 100,000, or at least 250,000, or at least 500,000, or at least 750,000 SNPs), with genotype imputation applied to increase the total number of genotyped DNA polymorphisms to at least $1.0 \times 10^6$, or at least $2.0 \times 10^6$, or at least $3.0 \times 10^6$, or at least $4.0 \times 10^6$, or at least $5.0 \times 10^6$, or at least $6.0 \times 10^6$, or at least $7.0 \times 10^6$, or at least $8.0 \times 10^6$, or at least $9.0 \times 10^6$, or at least $1.0 \times 10^7$, or at least $1.5 \times 10^7$, or at least $2.0 \times 10^7$.

The proportion or quantity of DNA contributed by the individual animals to the volume of milk can be determined herein, based on the bulk allele sampling of the DNA sequence polymorphisms in the milk, and the known allelic data for said DNA sequence polymorphisms in the individual animals. Hence, the composition of the DNA extracted from the milk can be determined in terms of the relative contribution of each animal (e.g., cow), i.e., what proportion of the DNA in the milk was contributed by animal 1, 2, 3, n. This can be accomplished using a variety of mathematical approaches generally known in the art, such as including least square analysis, non-negative least square analysis, weighted least square analysis, or maximum likelihood or Bayesian methods.

In certain embodiments, a linear model can be used. In certain embodiments, a set of linear equations can be defined containing a variable corresponding to the proportion of the DNA in the tank milk contributed by a given animal, and said proportion may be estimated by least square analysis of said equations.

For example, assuming bi-allelic polymorphisms each having a reference (R) allele and an alternate (A) allele (and hence, potential genotypes RR, RA or AA), a set of m linear equations can be defined of the form:

$$\widehat{BAF}_j = \Sigma_{j=1}^m f_i \times d_{ij} + \varepsilon_j$$

in which $f_i$ is the proportion of the DNA in the milk contributed by animal i, $d_{ij}$ is the "dosage" of the alternate allele A for animal i and polymorphism j, and $\varepsilon_j$ is the error term for polymorphism j. When allele sampling the milk by SWGS, $\widehat{BAF}_j$ corresponds to the proportion of A reads at the corresponding genome position.

For experimentally detected individual animal genotypes, $d_{ij}$ corresponds to 0, 0.5 or 1 for genotypes RR, RA and AA, respectively. For individual animal genotypes obtained by imputation, $d_{ij}$ is the dosage of the A allele estimated by a suitable imputation algorithm, such as the Beagle software package. For allele sampling in individual animals done by SWGS, $d_{ij} = 0.5 \times P(\text{"RA"}|nr_R, nr_A, q_j) + P(\text{"AA"}|nr_R, nr_A, q_j)$ where $nr_R$ (respectively $nr_A$) is the number of R (respectively A reads) for polymorphism j and animal i, and $q_j$ is the population frequency of the A allele of polymorphism j.

$$P(''RA'' | nr_R, nr_A, q_j) = \frac{2q_j(1-q_j) \times 0.5^{nr_R} \times 0.5^{nr_A} \times \frac{(nr_R + nr_A)!}{nr_R!}}{(1-q_j)^2 \times 1^{nr_R} \times 0^{nr_A} + 2q_j(1-q_j) \times 0.5^{nr_R} \times 0.5^{nr_A} \times \frac{(nr_R + nr_A)!}{nr_R!} + q_j^2 \times 0^{nr_R} \times 1^{nr_A}}$$

$$P(''AA'' | nr_R, nr_A, q_j) = \frac{q_j^2 \times 0^{nr_R} \times 1^{nr_A}}{(1-q_j)^2 \times 1^{nr_R} \times 0^{nr_A} + 2q_j(1-q_j) \times 0.5^{nr_R} \times 0.5^{nr_A} \times \frac{(nr_R + nr_A)!}{nr_R!} + q_j^2 \times 0^{nr_R} \times 1^{nr_A}}$$

The $f_i$'s can then be estimated by least square analysis, i.e., by minimizing $\Sigma_{j=1}^m \varepsilon_j^2$. When allele sampling in the milk is done by SWGS, a weighted least square analysis can be performed, i.e., $f_i$'s can be estimated by minimizing $\Sigma_{j=1}^m w_j \varepsilon_j^2$, where is the coverage ($nr_R + nr_A$).

Further, because somatic cells of the animal are the principal source of animal genomic DNA in its milk, the relative contribution of individual animals to the DNA in the pooled milk (e.g., tank milk) also replicates or reflects—and thus can be converted into—the relative contribution of the individual animals to the somatic cell concentration or somatic cell score (SCS) in the pooled milk. From there, the concentration of somatic cells in the milk of individual animals can be calculated or estimated, based on the proportion of the DNA contributed to the pooled milk by the individual animals, the actual concentration of somatic cells in the pooled milk (this is often determined by the dairy factories that are collecting the milk, as milk pricing is influenced by this parameter), and the relative contribution of the individual animals to the pooled milk in terms of individual volumes of milk (this information is generally available as present-day milking instrumentation automatically collects the amount of milk obtained from each animal such as cow). By means of an illustration, somatic cell score for individual animals i ($SCS_i$'s) can be calculated from the above-explained $f_i$'s as follows:

$$SCS_i = SCS_{tank} \times V_{tank} \times f_i / V_i,$$

where $V_{tank}$ is the total pooled volume of the milk (e.g., in litres) and $V_i$ is the volume of milk contributed by the individual animals i to the pooled milk, in the same unit (e.g., in litres). $V_i$ can either be measured directly, or can be estimated from the estimated yearly production of an animal and standard lactation curves capturing the evolution of the daily milk yield (or volume) during lactation, i.e., as a function of the number of days after calving.

Hence, in certain embodiments, the present methods may further comprise determining the concentration of somatic cells in the milk of the individual animals, based on the proportion or quantity of DNA contributed by the individual animals to the volume of milk. In certain embodiments, the concentration of somatic cells may be represented by a somatic cell score (SCS).

An increased concentration of somatic cells or increased SCS in the milk are characteristic features or signs of mastitis and subclinical mastitis. Mastitis involves an inflammation of the mammary gland. It may affect any mammal, non-ruminants and ruminants, such as cows, ewes, and goats. It is the most common and costly disease affecting dairy cows in the world. Mastitis typically results from udder infection caused by Gram-positive and Gram-negative bacteria. The main mastitis-causing pathogens include *Escherichia coli* (*E. coli*), *Streptococcus uberis* (*S. uberis*) and *Staphylococcus aureus* (*S. aureus*). Other organisms, less common, have also been identified as potential mastitis pathogens. Other bacteria causing bovine mastitis are without limitation *Streptococcus agalactiae, Klebsiella pneumoniae, Klebsiella oxytoca,* and *Pseudomonas aeruginosa*. These organisms are coined as major pathogens, most commonly associated with clinical mastitis in dairy cattle. They infect the udder cistern through the teat canal and induce inflammation of the milk-producing tissue with moderate to long lasting inhibition of milk secretion. When scar tissue is involved, a permanent reduction in the cow's milk production will occur. Mammary infection alters the composition, quantity, appearance and/or quality of the milk. Depending on the type of infection, common sources of microorganisms include unsanitary milking equipment, the milker, other animals, bedding, and the animals' own excreta (feces). The distinction between clinical and subclinical mastitis infections may hinge on whether or not (respectively) symptoms are visible to the naked eye, e.g., inspection by the farmer without the use of instrumentation or tests. Such symptoms may include udder swelling or redness and/or reduced or altered quality or quantity of produced milk.

Thus, in certain embodiments of the present methods, the concentration of somatic cells or the somatic cell score (SCS) in the milk of an individual animal above a predetermined threshold identifies said animal as having preclinical or clinical mastitis. In preferred embodiments, the concentration of somatic cells or SCS in the milk of an individual animal above a predetermined threshold may identify said animal as having preclinical mastitis. Hence, the present methods may be particularly useful and applied to detect or diagnose preclinical or clinical mastitis in the individual animals.

Such useful thresholds may depend on the species, subspecies, variety or breed of the animal, and will be generally known by the skilled artisan. By means of an example, for healthy cows the concentration of somatic cells or SCS in their milk is typically less than 100,000 cells/mL milk, whereas somatic cell concentrations or SCS of 200,000 cells/mL may be considered a workable threshold indicating cows with ≥200,000 cells/mL as having subclinical or clinical mastitis. Somatic cell concentrations or SCS in cows with clinical mastitis may typically reach millions cells/mL, by which time the cows may be excluded from milking.

In certain embodiments, the absolute quantity of DNA contributed by individual animals to the pooled milk can also be estimated, based on the proportion of the DNA contributed to the pooled milk by the individual animals, the actual concentration of DNA in the pooled milk, and the relative contribution of individual animals to the pooled milk in terms of individual volumes of milk.

In view of the above teachings, another aspect of the invention generally concerns a method for identifying an animal or animals having preclinical or clinical mastitis from a plurality of individual animals contributing milk to a volume of milk, the method comprising the steps of:
   a') determining the proportion or quantity of DNA contributed by the individual animals to the volume of milk by a method comprising allele sampling, such as low or ultralow allele sampling, of a plurality of DNA sequence polymorphisms across the genome in DNA extracted from a sample of the volume of milk by SWGS;
   b') determining the concentration of somatic cells in the milk of the individual animals, based on the proportion or quantity of DNA contributed by the individual animals to the volume of milk as determined in step a'); and
   c') identifying an animal or animals as having preclinical or clinical mastitis when the concentration of somatic cells in the milk of said animal or animals as determined in step b') exceeds a predetermined threshold.

The present application also provides aspects and embodiments as set forth in the following Statements:

Statement 1. A method for determining the proportion or quantity of DNA contributed by individual animals to a volume of milk collected from a plurality of individual animals, the method comprising the steps of:
   a) allele sampling for a plurality of DNA sequence polymorphisms in DNA extracted from a sample of the volume of milk by shallow whole genome sequencing (SWGS);
   b) determining the proportion or quantity of DNA contributed by the individual animals to the volume of milk, based on the allele sampling of said DNA sequence polymorphisms from step a), and allelic data for said DNA sequence polymorphisms in the individual animals.

Statement 2. The method according to Statement 1, wherein in step b) the allelic data for said DNA sequence polymorphisms in the individual animals comprises or consists of the genotypes or allelic dosages for said DNA sequence polymorphisms in the individual animals and/or SWGS-allele sampling data of said DNA sequence polymorphisms in the individual animals.

Statement 3. The method according to Statement 1 or 2, wherein the proportion of DNA contributed by the individual animals to the volume of milk is determined.

Statement 4. The method according to any one of Statements 1 to 3, further comprising determining the concentration of somatic cells in the milk of the individual animals, based on the proportion or quantity of DNA contributed by the individual animals to the volume of milk, for example wherein the concentration of somatic cells is represented by a somatic cell score (SCS).

Statement 5. The method according to any one of Statements 1 to 4, wherein the allele sampling of said DNA sequence polymorphisms by SWGS in step a) is low or ultralow allele sampling.

Statement 6. The method according to any one of Statements 2 to 4, wherein the SWGS-allele sampling data in the individual animals in step b) is from low or ultralow allele sampling by SWGS.

Statement 7. The method according to any one of Statements 1 to 6, wherein in step a) and/or step b) the sequencing depth of the SWGS is from 0.10 to 10.0, preferably from 0.25 to 5.0, such as at a sequencing depth of about 0.25, about 0.50, about 0.75, about 1.0, about 2.0, about 3.0, about 4.0 or about 5.0.

Statement 8. The method according to any one of Statements 1 to 6, wherein in step a) and/or step b) the sequencing depth of the SWGS is from 0.25 to 1.0, preferably about 0.25 or about 1.0.

Statement 9. The method according to any one of Statements 1 to 8, wherein the DNA sequence polymorphisms are single nucleotide polymorphisms (SNP).

Statement 10. The method according to any one of Statements 2 to 9, wherein the genotypes for said DNA sequence polymorphisms in the individual animals have been at least in part determined by genotyping arrays such as SNP genotyping arrays, by genome sequencing such as targeted genome sequencing or whole genome sequencing, or by any combination thereof.

Statement 11. The method according to Statements 10, wherein the genotypes for said DNA sequence polymorphisms in the individual animals have been at least in part determined by a SNP genotyping array capable of interrogating 100,000 or less SNPs, preferably 50,000 or less SNPs, more preferably 10,000 or less SNPs.

Statement 12. The method according to any one of Statements 2 to 11, wherein the genotypes or allelic dosages for said DNA sequence polymorphisms in the individual animals have been at least in part imputed.

Statement 13. The method according to any one of Statements 1 to 12, wherein at least $1 \times 10^5$, preferably at least $5 \times 10^5$, more preferably at least $1 \times 10^6$, even more preferably at least $5 \times 10^6$ or at least $8 \times 10^6$ DNA sequence polymorphisms are analysed.

Statement 14. The method according to any one of Statements 1 to 13, wherein the animals are lactating farm animals.

Statement 15. The method according to any one of Statements 1 to 14, wherein the animals are bovid or bovid hybrid; preferably bovine; more preferably cattle, such as *Bos taurus, Bos indicus* or hybrid cattle; or buffalo.

Statement 16. The method according to any one of Statements 1 to 14, wherein the animals are sheep or goats.

Statement 17. The method according to any one of Statements 1 to 16, wherein the volume of milk is tank milk.

Statement 18. The method according to any one of Statements 4-17, wherein the concentration of somatic cells or the somatic cell score (SCS) in the milk of an individual animal above a predetermined threshold identifies said animal as having preclinical or clinical mastitis.

Statement 19. A method for identifying an animal or animals having preclinical or clinical mastitis from a plurality of individual animals contributing milk to a volume of milk, the method comprising the steps of:
- a') determining the proportion or quantity of DNA contributed by the individual animals to the volume of milk by a method comprising allele sampling, such as low or ultralow allele sampling, of a plurality of DNA sequence polymorphisms in DNA extracted from a sample of the volume of milk by SWGS, preferably by the method of Statement 1;
- b') determining the concentration of somatic cells in the milk of the individual animals, based on the proportion or quantity of DNA contributed by the individual animals to the volume of milk as determined in step a'); and
- c') identifying an animal or animals as having preclinical or clinical mastitis when the concentration of somatic cells in the milk of said animal or animals as determined in step b') exceeds a predetermined threshold.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Materials and Methods
Simulated Data

Reference scheme (A): We simulated farms with n (25, 50, 100, 250, 500 and 1,000) cows contributing milk to the tank. Cows were genotyped with SNP arrays for m (10K, 50K, or 750K) markers without error. Minor Allele Frequencies (MAFs) were sampled from a uniform]0,0.5] distribution, and genotypes from the corresponding Hardy-Weinberg distributions. Somatic cell scores (SCS) of individual cows ($SCS_i$) were simulated by sampling values from a Weibull distribution with scale parameter $\alpha=1$ and shape parameter $\beta=2$, and multiplying the ensuing value by 200,000. Exact B-allele frequencies of individual SNPs ($BAF_j$) in the milk were determined for each SNP f based on the combination of cellular contribution of the n cows to the milk, and their genotype. It was assumed that B-allele frequencies were estimated with a normally distributed error N(0,0.0025) (i.e. SE=0.05), yielding m $\widehat{BAF_j}$.

Scheme B: Same setting as in the reference scheme with the following additions. For cows genotyped with the 10K or 50K arrays, we simulated imputation by augmenting the data to 8 million (M) genotypes using an error model mimicking real, MAF-dependent imputation accuracy. The error model was constructed using a real data set for 800 unrelated Holstein-Friesian individuals that were genotyped for an HD array of 777K SNP. This data set was split into a set of 200 and a set of 600 individuals. The set of 200 was reduced first to the genotypes interrogated by the 7K Illumina BovineLDv2.0 and then to the genotypes interrogated by the 50K Illumina BovineSNP50v3 SNP arrays. The reduced SNP sets were imputed back to the content of the Illumina BovineHD 777K SNP array using the 600 individuals as reference population. The frequencies of imputing a given genotype depending on the real genotype, were scored for MAF bins of 0.01 separately for the LD and 50K array data. We simulated allele sampling in tank milk by SWGS as follows. For each of the 8M SNP positions, we sampled local read depth (r∈integers) from a Poisson distribution with mean C, where C is the average genome-wide coverage (0.25, 0.5, 1, 2 or 5). We then sampled r reads, each with a probability=$BAF_j$ (computed as above) of being the B-allele.

Scheme C: Individual SNP genotypes and tank B-allele frequencies ($BAF_j$) were generated as in the reference scheme (genotypes at 8 M SNP positions). It was assumed that allele sampling in tank milk was done by SWGS at average coverage of C (0.25, 0.5, 1, 2 or 5) and allele sampling in cows was done by SWGS at average coverage of C (0.25, 0.5, or 1). Allele sampling in individual cows was simulated by (i) sampling, for each of 8M SNP positions, local read depth (r∈integers) from a Poisson distribution with mean C, and (ii) sampling r reads with probability 0, 0.5 or 1 to be the alternate allele (A) depending on the genotype of the cow (RR, RA or AA). Allele sampling in the tank milk was done as in Scheme B.

Real Data

Dataset 1: We obtained a sample of milk tank from a farm in France milking 133 Holstein-Friesian cows. All had been genotyped with a customised Illumina BovineLDv2 array interrogating 17K SNPs. For all cows, genotypes were imputed to HD (777K) density using a reference population of 800 Holstein-Friesian animals genotyped with the Illumina BovineHD array (777K SNPs) and the Beagle software (v3.3.2) (Browning & Browning 2009). Individual milk records, including volume and SCS (cells/mL), were obtained for all cows that had contributed milk to the tank. DNA was isolated from 1.5 ml tank milk using the NucleoMag® Blood kit (Macherey-Nagel, cat: 744501.1). The tank milk DNA was first genotyped using the customised Illumina BovineLDv2 interrogating 17K SNPs. An Illumina compatible NGS library was then prepared with 50 ng of genomic DNA using the KAPA HyperPlus kit (Roche, cat: KK8510). Sequencing was performed on a NextSeq500 instrument (Illumina), yielding 60 million paired end reads of 2*75 bp, corresponding to a genome coverage of around 3.5×. Reference (R) and alternate (A) alleles were counted at 777K SNP positions of the HD array using the BamReadCount tool (https://github.com/genome/bam-readcount.git), resulting in 699,402 positions covered with a least one read, at a mean coverage of 2.8. The read depth distribution resembled well a Poisson distribution with a mean of 2.8 (r=0.98) and 18% of the loci were covered with 1 read and 70% of the loci were covered with 2 or more reads.

Datasets 2 and 3: We obtained samples of tank milk from a Belgian farm including milk from respectively 520 and 120 Holstein-Friesian cows. Milk volume and SCS (cells/ml), were obtained for all cows that had contributed milk to the tank. All cows were genotyped with an Illumina BovineLDv2 array interrogating 17K SNPs using standard procedures, and imputed to whole genome using whole genome sequence data (average depth: 15×; range: 4×-48×) from 743 Holstein-Friesian animals as reference (M. Georges, unpublished) and the Beagle software (v5.0) (Browning et al. 2018) yielding allelic dosages for a total of 13 million SNPs. DNA extraction from the tank milk samples, genotyping with the Illumina BovineLDv2 (17K) and BovineSNP50v3 (50K) array, and sequencing (coverage 4×) were conducted as for dataset 1.

Dataset 4: In addition to obtaining a sample of tank milk on the day of the milk recording (i.e., yielding the SCS measured using with a cell counter) for the Belgian farm with 120 cows, we weekly collected an additional 11 tank milk samples before and 9 samples after, spanning a total period of about 3 months. The corresponding DNA samples were sequenced using the same procedures as for dataset 1.

Statistical Model

We defined a set of m linear equations of the form:

$$\widehat{BAF}_j = \Sigma_{j=1}^m f_i \times d_{ij} + \varepsilon_j$$

in which $f_i$ is the proportion of the DNA in the tank milk contributed by cow i, $d_{ij}$ is the "dosage" of the alternate allele A for cow i and marker j, and $\varepsilon_j$ is the error term for marker j. When genotyping the tank milk with arrays, $\widehat{BAF}_j$ corresponds to the B-allele frequency estimated by Genome Studio (Illumina). When allele sampling the tank milk by SWGS, $\widehat{BAF}_j$ corresponds to the proportion of A reads at the corresponding genome position. For cow genotypes obtained with arrays, $d_{ij}$ corresponds to 0, 0.5 or 1 for genotypes RR, RA and AA, respectively. For cow genotypes obtained by imputation, $d_{ij}$ is the dosage of the A allele estimated by Beagle (v3.3.2) (Browning & Browning 2009). For allele sampling in cows done by SWGS, $d_{ij}=0.5\times P("RA"|nr_R,nr_A, q_j)+P("AA"|nr_R,nr_A, q_j)$ where $nr_R$ (respectively $nr_A$) is the number of R (respectively A reads) for marker j and cow i, and q is the population frequency of the A allele of marker j.

$$P("RA"|nr_R,nr_A,q_j) = \frac{2q_j(1-q_j)\times 0.5^{nr_R}\times 0.5^{nr_A}\times \frac{(nr_R+nr_A)!}{nr_R!}}{(1-q_j)^2\times 1^{nr_R}\times 0^{nr_A}+2q_j(1-q_j)\times 0.5^{nr_R}\times 0.5^{nr_A}\times \frac{(nr_R+nr_A)!}{nr_R!}+q_j^2\times 0^{nr_R}\times 1^{nr_A}}$$

$$P("AA"|nr_R,nr_A,q_j) = \frac{q_j^2\times 0^{nr_R}\times 1^{nr_A}}{(1-q_j)^2\times 1^{nr_R}\times 0^{nr_A}+2q_j(1-q_j)\times 0.5^{nr_R}\times 0.5^{nr_A}\times \frac{(nr_R+nr_A)!}{nr_R!}+q_j^2\times 0^{nr_R}\times 1^{nr_A}}$$

For SNPs j without usable information for cow i (e.g., genotyping failure or no covering reads), $d_{ij}$ was set at $\widehat{BAF}_j$.

The $f_i$'s were estimated by least square analysis, i.e. by minimizing $\Sigma_{j=1}^m \varepsilon_j^2$. When allele sampling in the tank milk was done by SWGS, we also performed a weighted least square analysis, i.e. we estimated $f_i$'s by minimizing $\Sigma_{j=1}^m w_j\varepsilon_j^2$, where $w_j$ is the coverage ($nr_R+nr_A$).

The $SCS_i$'s were calculated from the $f_i$'s $$SCS_i = SCS_{tank}\times V_{tank}\times f_i/V_i$$

Where $V_{tank}$ and $V_i$ are the volume of milk in the tank (e.g., in litres) and the volume of milk contributed by cow i to the tank (in the same unit, such as in litres), respectively. $V_i$ can either be measured directly, since some milking machines record that information. If the actual values of $V_i$ are not known (e.g., because the milking machines that are used on the farm do not provide that information), $V_i$ can be estimated from the estimated yearly production of the cow and standard lactation curves expressing the evolution of the daily milk yield (or volume) during lactation, i.e., as a function of the number of days after calving.

The accuracies of the predictions were measured by (i) the Pearson's correlation (r) between real and estimated $SCS_i$, and/or (ii) the ability to discriminate animals with SCS above versus below a certain threshold value measured as $(T_P+T_N)/m$, where $T_P$ stands for the number of true positives, $T_N$ for the number of true negatives, and m for the total number of cows.

To test the effect of sequence depth on accuracy we sampled reads overlapping SNP positions with probability x, such that $E(C\times x)$ D, where D is the desired sequence depth.

Results

Simulated Data

We first re-evaluated the accuracy in estimating the number of SCS for individual cows by bulk genotyping of tank milk under the "reference scheme" (A), i.e., by assuming that individual cows and the tank milk are genotyped with the same of the three most commonly used bovine SNP arrays interrogating respectively 10K, 50K or 750K SNPs. As can be seen from FIG. 2A, with 10K SNPs the accuracies of the predictions are satisfactory (r≥0.9) for farms with ≤100 cows, with 50K SNPs for farms with ≤250 cows, and with 750K SNPs for farms with up to 1,000 cows contributing milk to a single tank. Yet genotyping entire herds with 50K, let alone 750K arrays, is at present prohibitively expensive.

Figure 2:
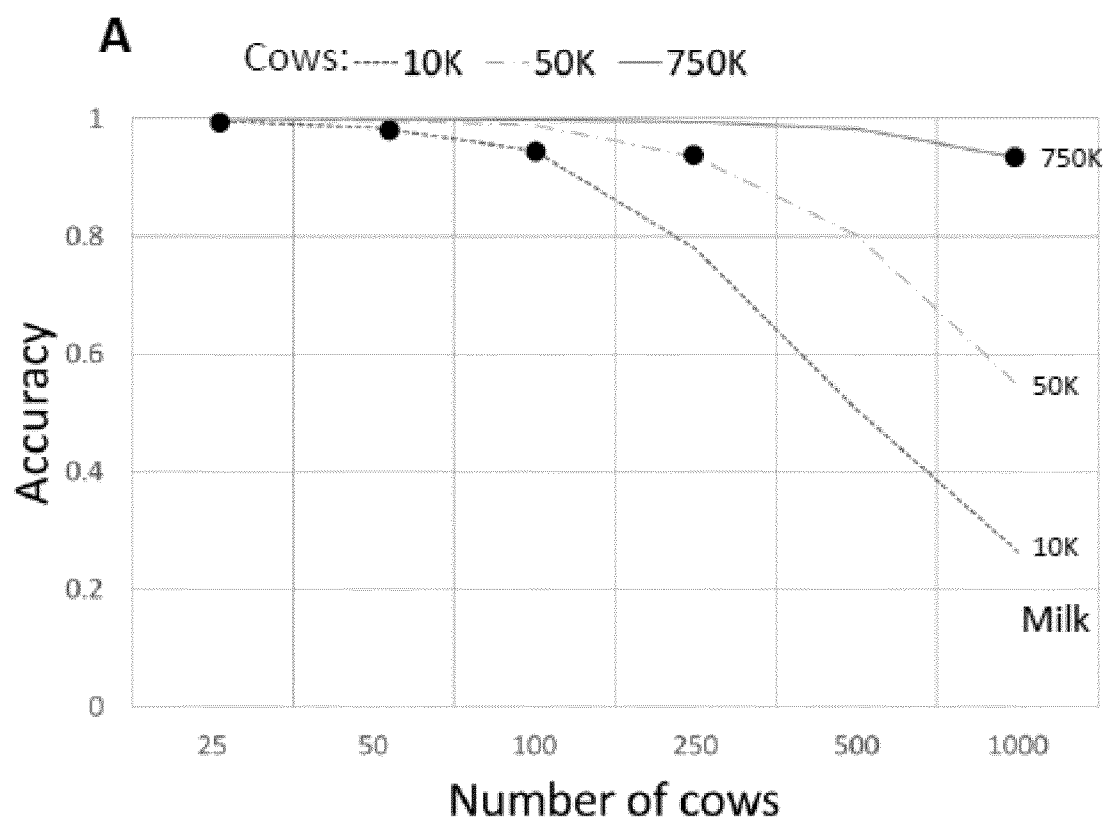
FIG. 2 illustrates accuracy in estimating somatic cell score (SCS) for individual cows by bulk DNA analysis of tank milk using three different schemes: (A) SNP arrays for genotyping DNA polymorphisms both in tank milk and in individual cows contributing to the tank milk (reference scheme "A"); (B) SWGS for allele sampling for DNA polymorphisms in tank milk and SNP arrays for genotyping DNA polymorphisms in individual cows contributing to the tank milk (scheme "B", embodying the principles of the invention); (C) SWGS for allele sampling for DNA polymorphisms both in tank milk and in individual cows contributing to the tank milk (scheme "C", embodying the principles of the invention).
Figure 2:
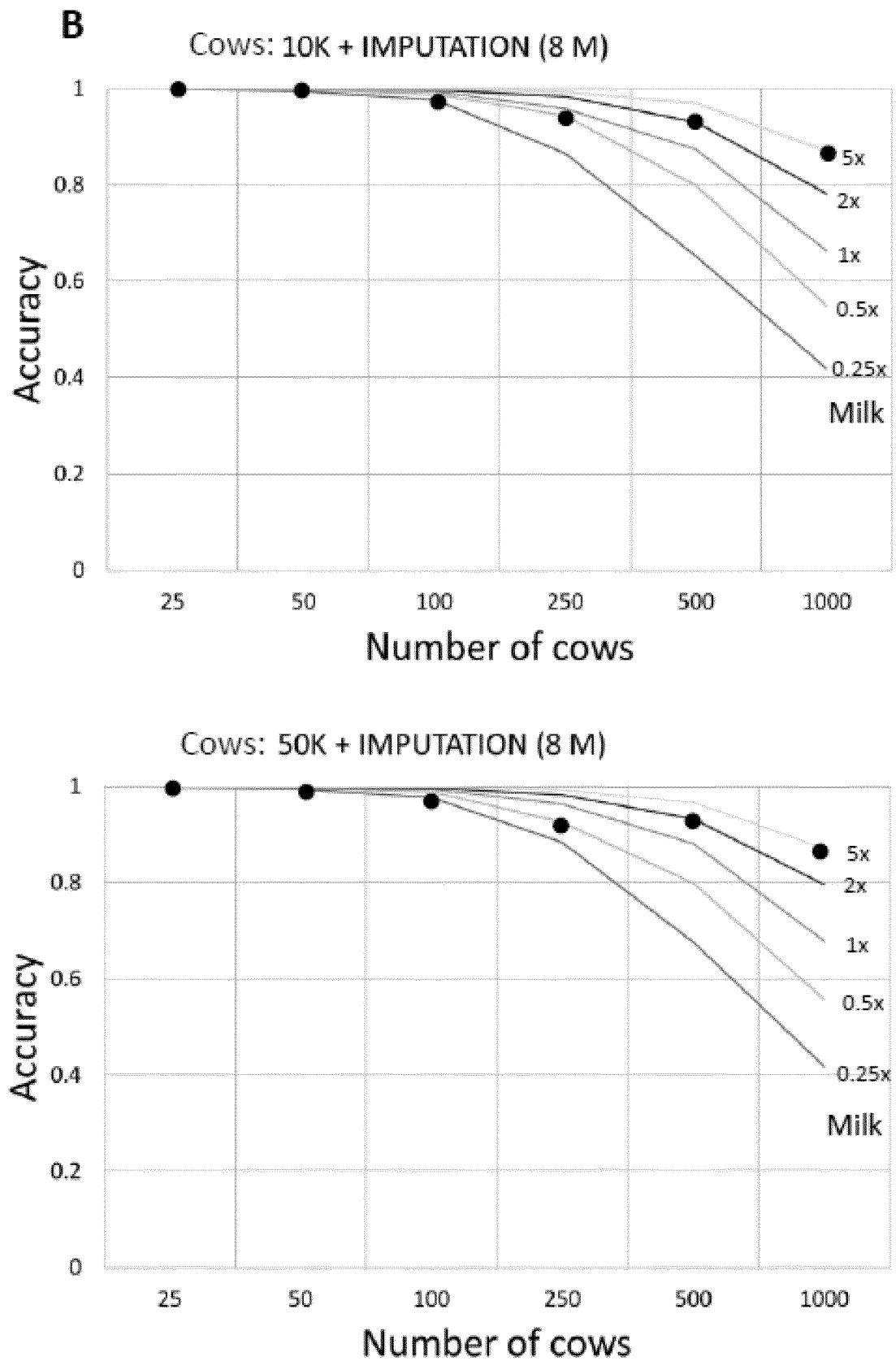
Figure 2:
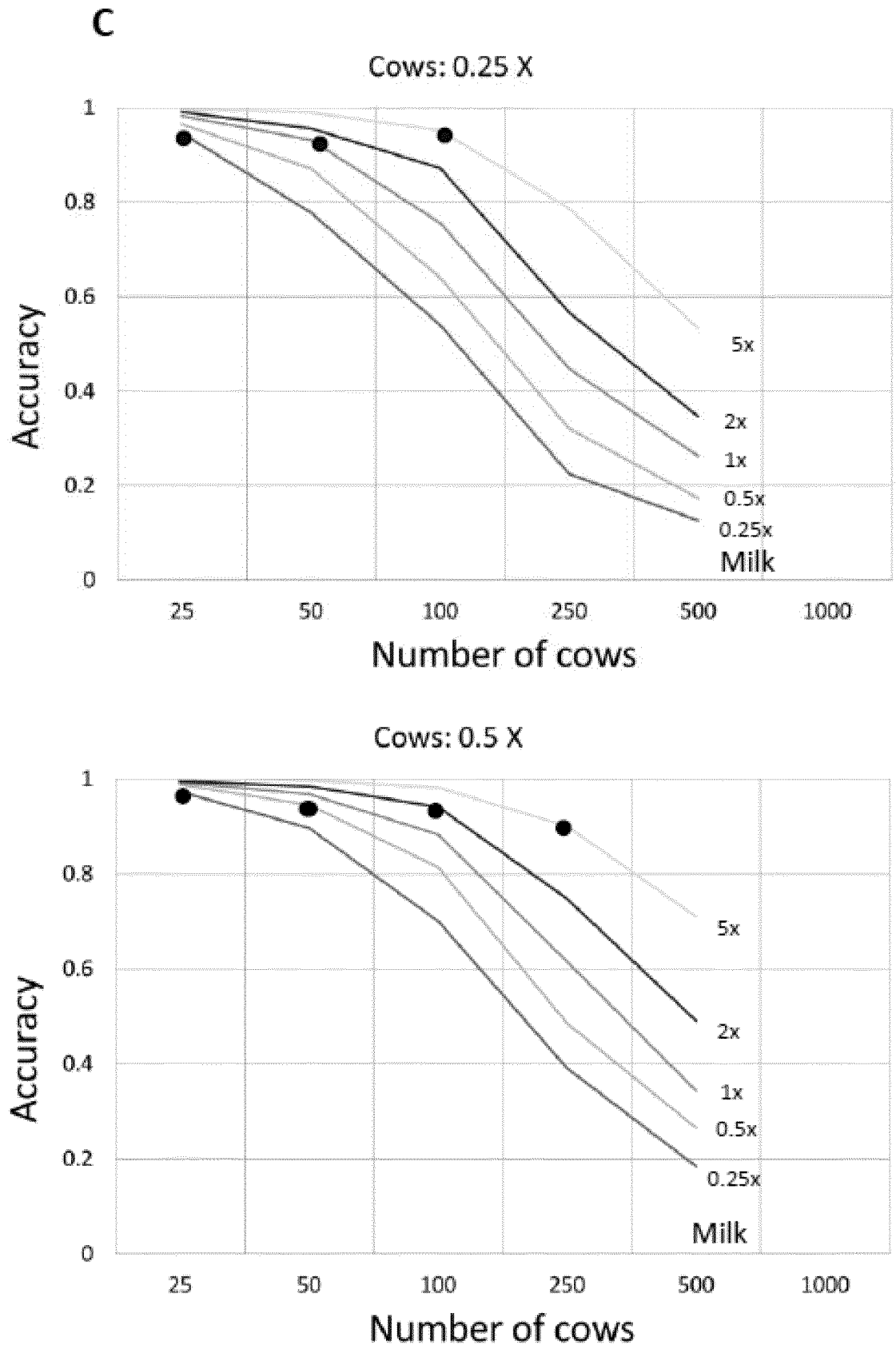
Figure 2:
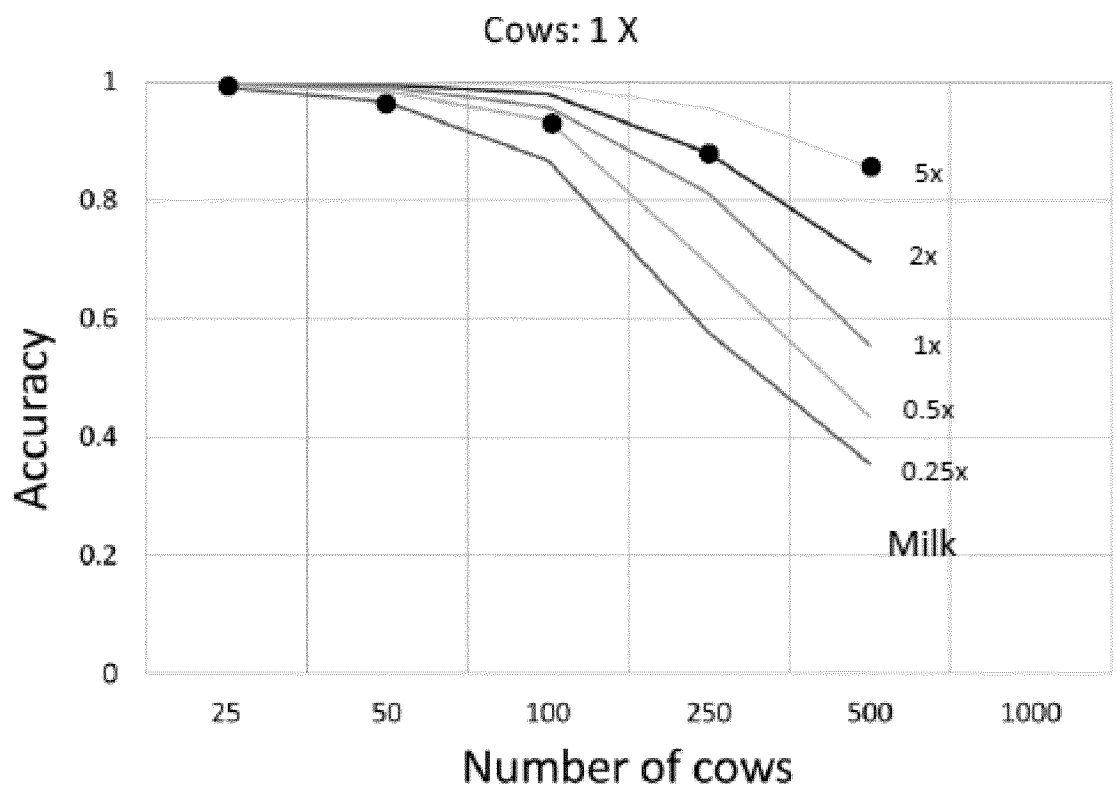

We therefore explored a first set of alternative schemes (B), in which (i) individual cows are genotyped with either the 10K, 50K or 750K SNPs, and genotypes augmented to 8 million (8M) SNPs by imputation, while (ii) allele sampling in the tank milk is done by SWGS at sequence depths ranging from 0.25 to 5. FIG. 2B shows at first that the accuracy of the predictions is only marginally affected by the type of SNP array that is used, i.e., 10K SNP arrays are performing as well as the 50K and 750K arrays (not shown). Most importantly, a sequence depth (for the tank milk) of 0.25 is sufficient to provide a satisfactory accuracy for farms with ≤100 cows, a sequence depth of 0.5 for farms with ≤250 cows, a sequence depth of 2 for farms with ≤500 cows, and a sequence depth of 5 for farms with ≤1,000 cows.

We further considered a third set of schemes (C), in which allele sampling in both tank milk and individual cows is done by SWGS. As can be seen from FIG. 2C, a sequence depth of 0.25× for milk and cows would be sufficient for farms with 25 cows. If keeping the sequence depth for cows at 0.25×, the depth for the milk would preferably be increased to 1× and 5× for farms with 50 and 100 cows, respectively. To be applicable in farms with 250 cows, the sequence depth for the cows would preferably be increased to 0.5× and for milk to 5×.

Real Data

Figure 3:
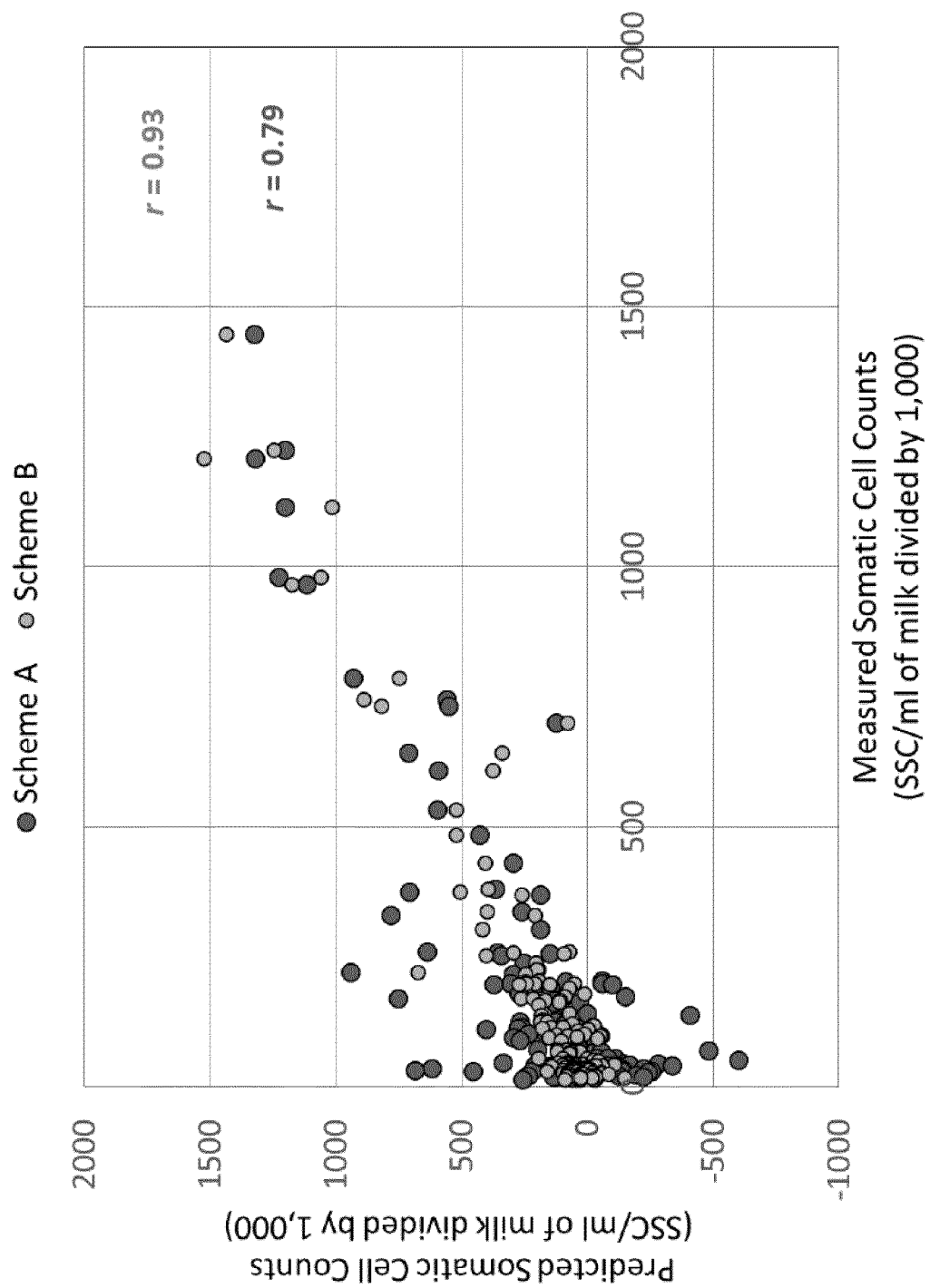
FIG. 3 illustrates correlation between predicted and measured SCS for individual cows using two different genotyping schemes: SNP arrays for genotyping DNA polymorphisms both in tank milk and in individual cows contributing to the tank milk (reference scheme "A"); SWGS for allele sampling for DNA polymorphisms in tank milk and SNP arrays and in silico imputation for genotyping DNA polymorphisms in individual cows contributing to the tank milk (scheme "B", embodying the principles of the invention).

SCS for the 133 milking cows was first estimated under the "reference" scenario (A), i.e. using only the genotypes of the 17K SNP interrogated by the Illumina LD array. The correlation between real and estimated SCS was 0.91. We then repeated the computations under scheme B, i.e. using the imputed genotype dosages at 777 K SNP positions (covered by the Illumina HD array) for the cows, and the B-allele frequencies at the corresponding positions for the milk estimated from SWGS data as described in Materials and Methods (3.5× coverage). The accuracy of the predicted SCS increased to 0.96. Visual examination of the correlation plots revealed one cow with >3 million SSC/ml (i.e. with overt mastitis), which would have inflated the r'-values. We removed this outlier and repeated the analyses. The correlation between real and estimated SCS was 0.79 under scheme A, i.e. when using only the information from the 17K SNPs interrogated by the LD array, and increased to 0.93 under scheme B, i.e. adding information from imputed genotypes in the cows and SWGS of the milk (FIG. 3). This clearly demonstrated the superiority of scheme B over A.

Figure 4:
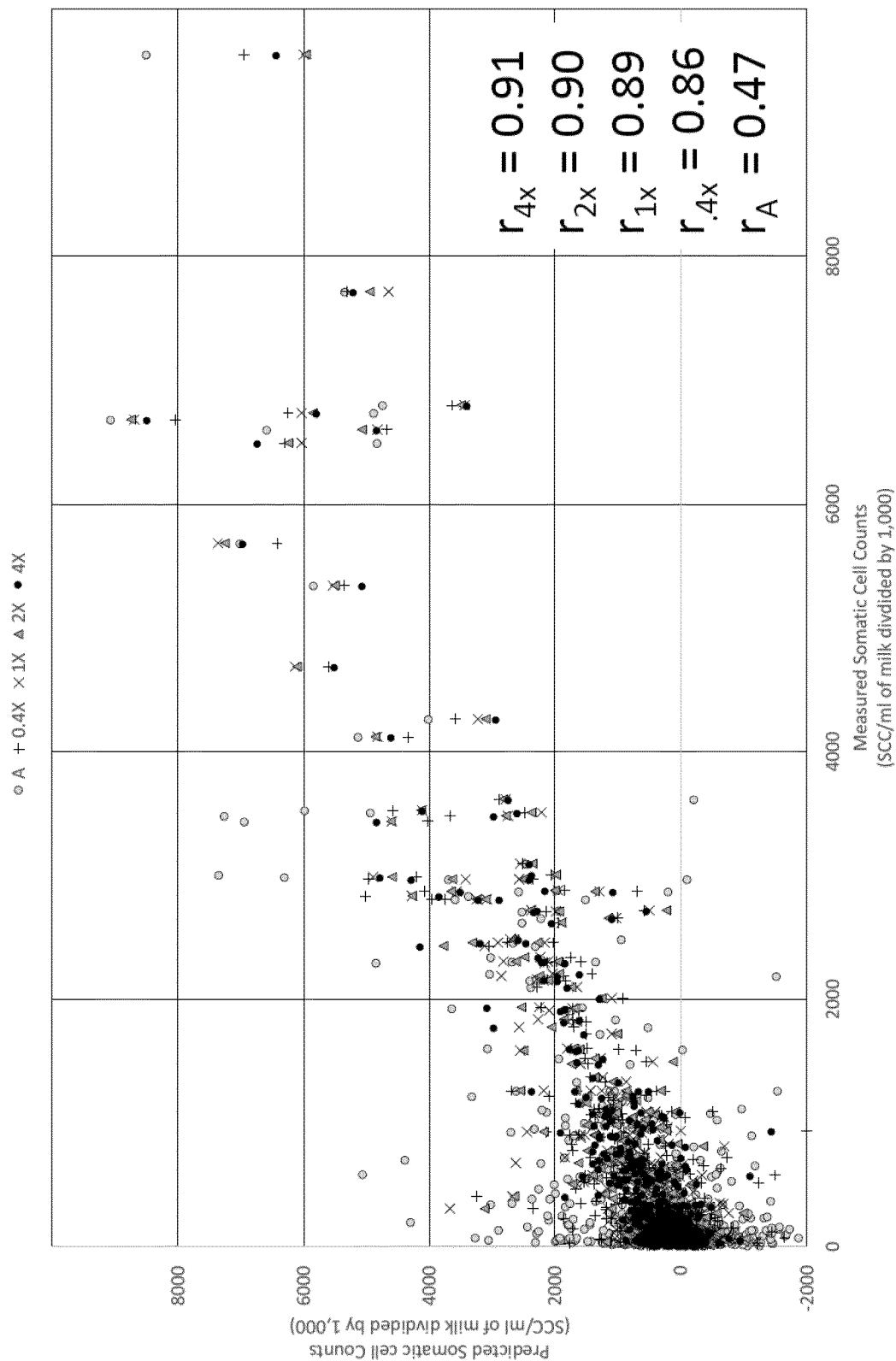
FIG. 4 illustrates correlation between predicted and measured SCS for individual cows using two different genotyping schemes: SNP arrays for genotyping DNA polymorphisms both in tank milk and in individual cows contributing to the tank milk (reference scheme "A"); SWGS at various depths (0.4×, 1×, 2×, 4×) for allele sampling for DNA polymorphisms in tank milk and SNP arrays and in silico imputation for genotyping DNA polymorphisms in individual cows contributing to the tank milk (scheme "B", embodying the principles of the invention).

We then tested the effect of augmenting the number of cows contributing milk to tank milk using dataset 2 (520 cows). Under scheme A, i.e., milk and cows genotyped with SNP arrays, the correlation between predicted and measured SCC dropped to 0.47 (FIG. 4), as predicted by the simulations. We then applied scheme B, i.e., imputing the cows to >10M SNPs and performing whole genome sequencing on the milk. The correlation increased to 0.91 when using all available sequence information, i.e. at 4× sequence depth. We down-sampled the sequence data to 2×, 1× and 0.4× depth. The correlation did not drop below 0.86 at 0.4× coverage.

Figure 5:
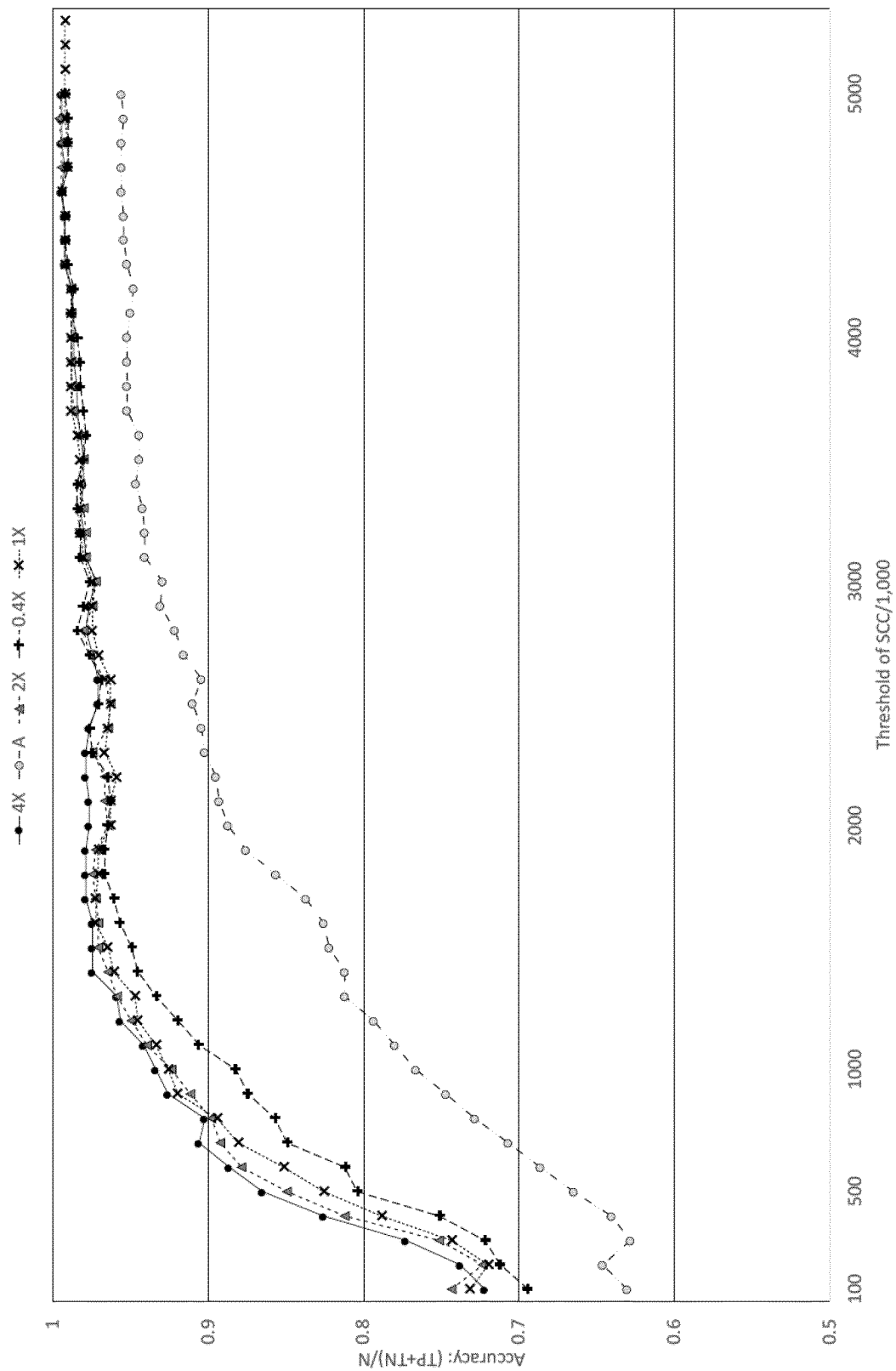
FIG. 5 illustrates accuracy of discriminating animals with SCS above versus below a chosen threshold value using two different genotyping schemes: SNP arrays for genotyping DNA polymorphisms both in tank milk and in individual cows contributing to the tank milk (reference scheme "A"); SWGS at various depths (0.4×, 1×, 2×, 4×) for allele sampling for DNA polymorphisms in tank milk and SNP arrays and in silico imputation for genotyping DNA polymorphisms in individual cows contributing to the tank milk (scheme "B", embodying the principles of the invention).

Farmers typically use a select SCS threshold value above which they would intervene, such as for example using antibiotic treatment. We therefore also evaluated the accuracy of our method in discriminating animals with SCS above versus below a chosen threshold value. Using a commonly used value of 1 million SCS as threshold, scheme B had an accuracy of ≥0.9, even when sequencing the milk at 0.4× depth (FIG. 5). Taken together these results demonstrate the efficacy of the proposed scheme B in detecting cows with subclinical mastitis even for very large farms. Indeed, genotyping cows with a 17K array, combined with genotype imputation of the cows to whole genome and shallow (e.g., 0.4×) sequencing of the tank milk is advantageously informative and cost-effective proposition.

Figure 6A:
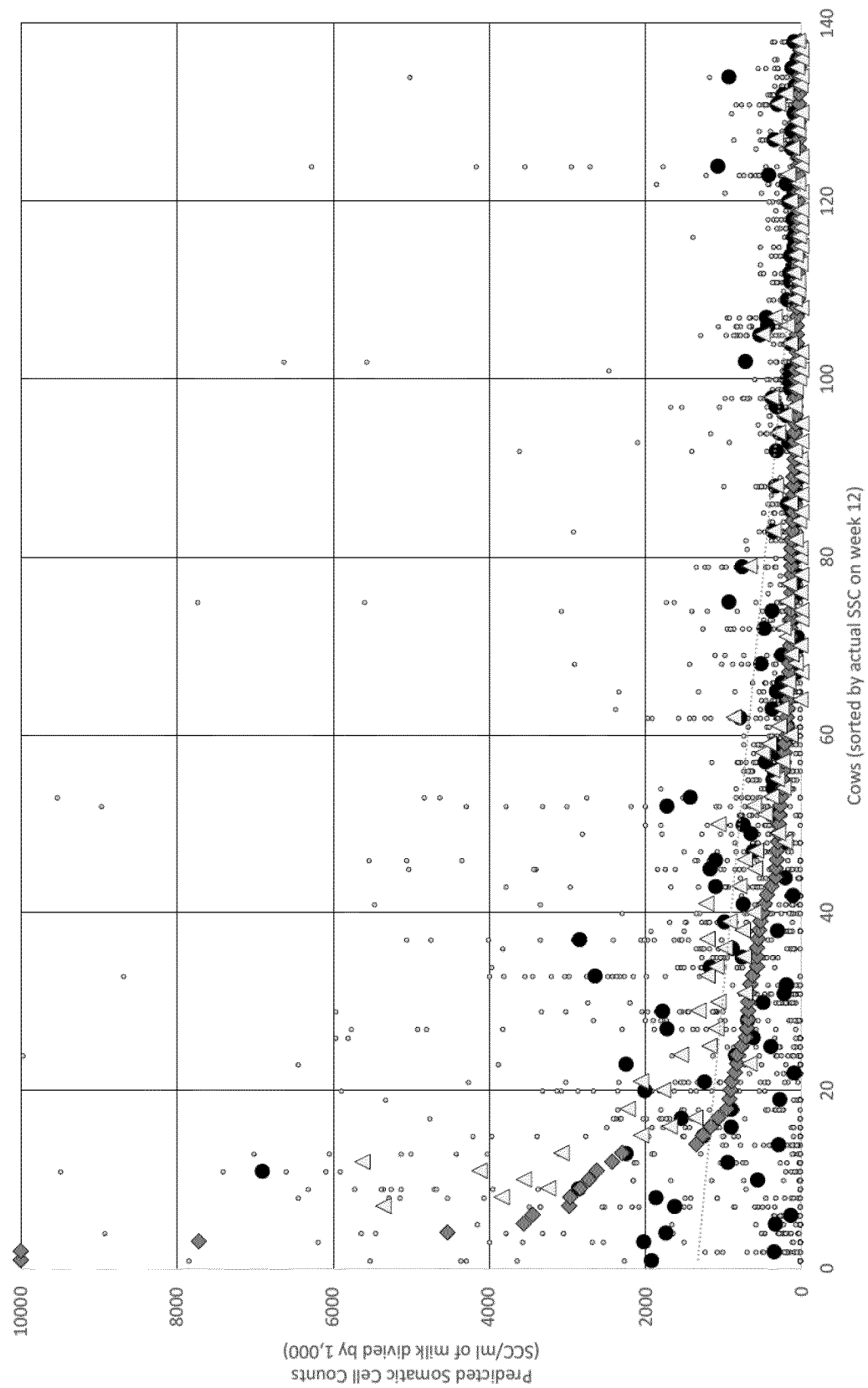
FIG. 6 illustrates (A) estimation of SCS in the milk of 120 cows over a 21-week period (diamonds: SCS measured at week 12; triangles: SCS predicted by bulk genotyping by sequencing of tank milk on week 12; large circles: average predicted SCS over the 21 weeks; small circles dots: individual measurements); (B) correlation between measured SCS on week 12 and average predicted SCS over the 21 week period.
Figure 6:
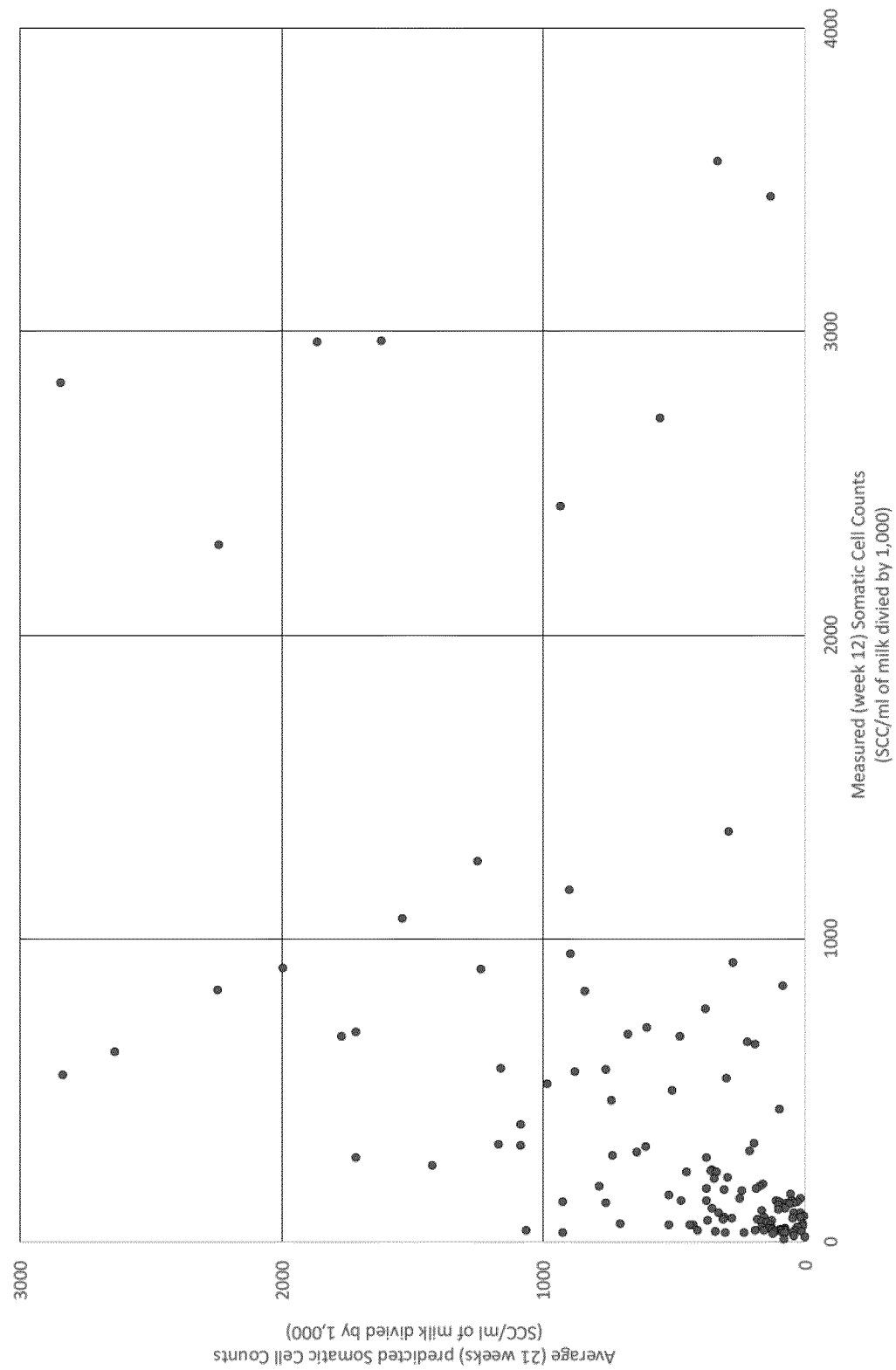

We finally wanted to use the proposed method to monitor the evolution of SCS for individual at weekly intervals over a period of three months. We collected tank milk samples from a farm with 120 cows (dataset 4) for 21 consecutive weeks. Actual SCS were measured on individual cows at week 12. The results indicated that the SCS measured at week 12 were a poor predictor (r=0.56) of the average predicted SCS over an about 3-month period centred around week 12. Indeed, some cows with high measured SCS at week 12 had overall very acceptable SCS over the 3 month period, while some cows with low measured SCS at week 12 had on average high to very high SCS over the 3-month period (FIG. 6A, B). This analysis thus demonstrated that quarterly milk recording is a relatively poor indicator of an animal's actual SCS in the interval between milk recordings, and the actual average SCS may be grossly under- or over-estimated. Moreover, it appears that clinical manifestation does not necessarily correlate well with SCS: cows with very high SCS may be completely symptomless and their milk added to the tank milk thus detracting from its quality and value. These facts further underscore the importance and improved informative value of the genetic analysis protocols taught by the present application for detection of subclinical mastitis in animals.

CITATION LIST

Blard et al. J. Dairy Sci. 2012, vol. 95:4109-4113
Browning & Browning. Am J Hum Genet 2009, vol. 84, 210-223
Browning et al. Am J Hum Genet 2018, vol. 103, 338-348
Hogeveen et al. N. Z. Vet. J. 2011, vol. 59, 16-23
Howie et al. Nat Genet. 2012, vol. 44, 955-9
Li et al. Genet Epidemiol. 2010, vol. 34, 816-34
Marchini & Howie. Nat Rev Genet 2010, vol. 11, 499-511
Niedringhaus et al. Anal Chem. 2011, vol. 83: 4327-4341
Sambrook and Russell, Molecular Cloning: A Laboratory Manual, the third edition, Cold Spring Harbor Laboratory Press, Cold Spring Harbor, New York, 1.31-1.38, 2001
Sharma. BioTechniques. 1993, vol. 14, 176-178
Sims et al. Nat. Rev. Gen. 2014, vol. 15, 121-132

The invention claimed is:

1. A method for determining the proportion or quantity of DNA contributed by individual animals to a volume of milk collected from at least 100 individual animals, the method comprising the steps of:
   a) allele sampling for a plurality of DNA sequence polymorphisms in DNA extracted from a sample of the volume of milk by shallow whole genome sequencing (SWGS), wherein the sequencing depth of the SWGS is 10 or less and wherein the plurality of DNA sequence polymorphisms comprises at least $1 \times 10^5$ DNA sequence polymorphisms;
   b) determining the proportion or quantity of DNA contributed by the individual animals to the volume of milk, based on the allele sampling of said DNA sequence polymorphisms from step a), and allelic data for said DNA sequence polymorphisms in the individual animals.

2. The method according to claim 1, wherein in step b) the allelic data for said DNA sequence polymorphisms in the individual animals comprises or consists of the genotypes or allelic dosages for said DNA sequence polymorphisms in the individual animals and/or SWGS-allele sampling data of said DNA sequence polymorphisms in the individual animals.

3. The method according to claim 2, wherein the genotypes for said DNA sequence polymorphisms in the individual animals are determined by genotyping arrays, by genome sequencing, or by any combination thereof and/or the genotypes or allelic dosages for said DNA sequence polymorphisms in the individual animals are imputed.

4. The method according to claim 3, wherein the genotypes for said DNA sequence polymorphisms in the individual animals are determined by a SNP genotyping array capable of interrogating 100,000 or less SNPs.

5. The method according to claim 3, wherein the genotyping arrays are SNP genotyping arrays.

6. The method according to claim 3, wherein the genome sequencing is targeted genome sequencing or whole genome sequencing.

7. The method according to claim 2, wherein the SWGS-allele sampling data in the individual animals in step b) is from low or ultralow allele sampling by SWGS.

8. The method according to claim 2, wherein in step b) the sequencing depth of the SWGS is from 0.10 to 10.0.

9. The method according to claim 1, further comprising determining the concentration of somatic cells in the milk of the individual animals, based on the proportion or quantity of DNA contributed by the individual animals to the volume of milk.

10. The method according to claim 1, wherein the allele sampling of said DNA sequence polymorphisms by SWGS in step a) is low or ultralow allele sampling.

11. The method according to claim 1, wherein in step a) the sequencing depth of the SWGS is from 0.10 to 10.0.

12. The method according to claim 11, wherein the sequencing depth of the SWGS is from 0.25 to 5.0.

13. The method according to claim 12, wherein the sequencing depth of the SWGS is from 0.25 to 1.0.

14. The method according to claim 1, wherein the DNA sequence polymorphisms are single nucleotide polymorphisms (SNP).

15. The method according to claim 1, wherein the plurality of DNA sequence polymorphisms comprises at least $1\times10^6$ DNA sequence polymorphisms.

16. The method according to claim 1, wherein the animals are lactating farm animals.

17. The method according to claim 16, wherein the animals are bovid or bovid hybrid.

18. The method of claim 17, wherein the animal is bovine.

19. The method of claim 18, wherein the bovine is cattle or buffalo.

20. The method of claim 19, wherein the cattle is *Bos taurus*, *Bos indicus* or hybrid cattle.

21. The method according to claim 16, wherein the animals are sheep or goats.

22. The method according to claim 1, wherein the volume of milk is tank milk.

23. A method for identifying an animal or animals having preclinical or clinical mastitis from at least 100 individual animals contributing milk to a volume of milk, the method comprising the steps of:
  a') determining the proportion or quantity of DNA contributed by the individual animals to the volume of milk by a method comprising allele sampling of a plurality of DNA sequence polymorphisms in DNA extracted from a sample of the volume of milk by SWGS, wherein the sequencing depth is 10 or less and wherein the plurality of DNA sequence polymorphisms comprises at least $1\times10^5$ DNA sequence polymorphisms;
  b') determining the concentration of somatic cells in the milk of the individual animals, based on the proportion or quantity of DNA contributed by the individual animals to the volume of milk as determined in step a'); and
  c') identifying an animal or animals as having preclinical or clinical mastitis when the concentration of somatic cells in the milk of said animal or animals as determined in step b') exceeds a predetermined threshold.

* * * * *